US010376603B2

(12) United States Patent
Montclare et al.

(10) Patent No.: US 10,376,603 B2
(45) Date of Patent: Aug. 13, 2019

(54) ENGINEERED FLUORINATED BIOMATERIALS

(71) Applicant: New York University, New York, NY (US)

(72) Inventors: Jin Kim Montclare, New York, NY (US); Joseph A. Frezzo, Brooklyn, NY (US); Cynthia Xu, Bridgewater, NJ (US); Youssef Zaim Wadghiri, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/212,599

(22) Filed: Jul. 18, 2016

(65) Prior Publication Data

US 2017/0014351 A1 Jan. 19, 2017

Related U.S. Application Data

(60) Provisional application No. 62/193,852, filed on Jul. 17, 2015.

(51) Int. Cl.

| | |
|---|---|
| ***A61K 9/51*** | (2006.01) |
| ***A61K 47/42*** | (2017.01) |
| ***A61K 47/64*** | (2017.01) |
| ***A61K 49/14*** | (2006.01) |
| ***A61K 51/08*** | (2006.01) |
| ***C07K 14/78*** | (2006.01) |
| ***A61K 31/704*** | (2006.01) |

(52) U.S. Cl.

CPC ............ *A61K 51/08* (2013.01); *A61K 9/5169* (2013.01); *A61K 31/704* (2013.01); *A61K 47/42* (2013.01); *A61K 47/6435* (2017.08); *A61K 49/14* (2013.01); *C07K 14/78* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 2013/0102993 A1* | 4/2013 | Kim | ........................ | A61K 9/127 604/500 |
| 2013/0331465 A1* | 12/2013 | Montclare | .............. | C07K 14/00 514/773 |

OTHER PUBLICATIONS

Dai et al. "Artificial Protein Block Polymer Libraries Bearing Two SADs: Effects of Elastin Domain Repeats," Biomacromolecules 2011, 12, 4240-4246 (Year: 2011).*

Montclare et al. "Biosynthesis and Stability of Coiled-Coil Peptides Containing (2S,4R)-5,5,5-Trifluoroleucine and (2S,4S)-5,5,5-Trifluoroleucine," ChemBioChem 2009, 10, 84-86 (Year: 2009).*

Wang et al. "The Functions and Applications of RGD in Tumor Therapy and Tissue Engineering," Int. J. Mol. Sci. 2013, 14, 13447-13462 (Year: 2013).*

MacEwan et al. "Applications of elastin-like polypeptides in drug delivery," Journal of Controlled Release 190 (2014) 314-330 (Year: 2014).*

* cited by examiner

*Primary Examiner* — Christina Bradley

(74) *Attorney, Agent, or Firm* — Hodgson Russ LLP

(57) ABSTRACT

Provided are protein polymers providing the dual functionality of delivery and imaging. The protein polymers comprise a coiled-coil domain of the cartilage oligomeric matrix protein and repeats of elastic like peptides. The coiled-coil domain allows delivery of molecules, the elastin-like peptide domain provides thermo-responsive functionality, and a plurality of leucine residues, which can be fluorinated, provide imaging functionality.

22 Claims, 12 Drawing Sheets

Specification includes a Sequence Listing.

MRGSHHHHHH GSACETflAARG DATATATATA ACGDTflAPQMTfl RETflQETNAATfl

60 70 80 90 100 110

QDVRETflTflRQQ VKEITflKNT VMESDASGTflQ AARGDATATA TATAVDKPIA ASAVPGVGVP 120 130 140 150 160

GVGVPGFGVP GVGVPGVGVP GVGVPGVGVP GFGVPGVGVP GVGVPTflEGSG TGAKTflN

ENGINEERED FLUORINATED BIOMATERIALS

CROSS-REFERENCE TO RELATED APPLICATIONS

This application claims priority to U.S. Provisional application No. 62/193,852, filed on Jul. 17, 2015, the disclosure of which is incorporated herein by reference.

STATEMENT REGARDING FEDERALLY SPONSORED RESEARCH

This invention was made with government support under grant no. DMR-1205384 awarded by the National Science Foundation, and 5P30CA016087-32 awarded by the National Cancer Institute of the National Institutes of Health. The government has certain rights in the invention.

BACKGROUND OF THE DISCLOSURE

Many existing technologies rely on synthetic materials such as fluorinated lipids, emulsions and crown ethers to generate the fluorine signal in NMR. These technologies are good sources of fluorine signaling, especially for quantitative tissue oxygenation measurements. However, the toxicities and uncertainty of breadth of function associated with these materials have hampered their use. There are also classes of $^{19}F$ MRI contrast agents being developed that harbor "smart" stimuli responsive capabilities to sense the appearance of biomarkers of diseases or changes in pH, metal ion concentration and partial pressure of oxygen ($pO_2$) (Yu et al., Curr Med Chem 2005, 2:819-848; Senanayake et al., Chem. Commun., 2007, 2923-2925; Prior et al., In Vivo Magnetic Resonance Spectroscopy III: In Vivo MR Spectroscopy: Potential and Limitations. Vol. 28. Springer-Verlag; Berlin: 1992. p. 101-130; Deutsch et al., Biophys. J 1989, 55:799-804, Griffiths et al., NMR Biomed 1999; 12:495-504; Metcalfe et al., Cell Calcium 1985; 6:183-195; Mehta et al., Bioconjugate Chemistry, 1994, 5:257-261; Mehta et al., Bioconjugate Chemistry, 1994, 5:257-261). However, these contrast agents, while providing imaging functionality, are not capable of assisting with drug delivery.

SUMMARY OF THE DISCLOSURE

The present disclosure provides compositions and methods for delivery of therapeutic and/or diagnostic agents. The compositions can perform dual functions of delivery and imaging. Thus, delivery of molecules can be tracked. Encapsulated agents can be released by increasing the temperature. The composition comprises a protein polymer carrier, which comprises a coiled coil domain of the cartilage oligomeric matrix protein (COMPcc domain or COMPcc sequence) and one or more elastin like peptide domains. The polymer carrier may further comprise one or more of the following: polyhistidine tag, integrin-binding sties (e.g., RGD), AT rich sequences, and leucine residues which can be fluorinated. The polymer carrier may also comprise residual amino acids from cloning.

For example, the polymer carrier comprises a COMPcc sequence, an elastin-like peptide sequence, and a linker sequence between the COMPcc sequence and the elastin-like peptide sequence. In one example, the polymer carrier comprises an amino acid sequence, which from the N- to the C-terminus, comprises the following blocks: N-terminal sequence[Linker 1 sequence]-[COMPcc domain sequence]-[Linker 2 sequence]-[Elastin-like peptide domain sequence]. The N-terminal sequence represents cloning residues or residues added to aid in purification. For example, the N-terminal sequence can comprise methionine, polyhistidine sequence, and GS, which is frequently added in plasmids for purification via antibodies. The Linker 1 sequence can comprise integrin-binding tripeptide (RGD), AT repeats and residual amino acids from cloning. The COMPcc domain sequence is a coiled-coil domain of COMP (also referred to herein as the C domain), and has the sequence of wild type COMPcc (SEQ ID NO:3) or a variant thereof. The Linker 2 sequence is present between the COMPcc domain sequence and the elastin-like peptide domain sequence and comprises at least 1 to 3 amino acids. For example, it can comprise an integrin binding tripeptide (RGD), AT repeats and residual amino acids from cloning. The elastin-like peptide domain sequence comprises repeats of the sequence VPGXG (SEQ ID NO:15). For example, the elastin-like peptide domain can have the sequence $[(VPGXG)_2VPGXG(VPGXG)_2)]_n$ (SEQ ID NO:30), which can be represented as $[$(SEQ ID NO:15)$_n$ SEQ ID NO:15 (SEQ ID NO:15)$_n]$ wherein n can be from 1 to 24 and X can be any amino acid other than proline. The E domain sequence can additionally have 1-3 residual amino acids such as VP. The polymer carrier can optionally also comprise a C-terminal sequence.

The polymer carrier has multiple leucine residues. These are present in the COMPcc domain sequence and can also be present elsewhere. For example, the polymer carrier shown in FIG. 1 has 11 leucine residues. For any polymer of the present disclosure, one or more of the leucines can be fluorinated. Fluorinated leucines at each location, can independently be: not fluorinated, monofluorinated, difluorinated, trifluorinated, tetrafluorinated, pentafluorinated or hexafluorinated. In the sequence shown in FIG. 1, there is 1 leucine in Linker 1, 7 leucines in the COMPcc domain sequence, 1 leucine in Linker 2, and 2 leucines in the C-terminal sequence. In the example shown in FIG. 1, all the leucines are shown as trifluorinated.

The present disclosure provides a method for delivery of agents and/or imaging of the polymer carrier of the present disclosure, which acts as a delivery agent. The method comprises encapsulating an agent in the polymer carrier, administering to an individual in need thereof, a composition comprising the polymer carrier having encapsulated therein an agent of interest, and allowing delivery of the agent to desired sites, or applying increased temperature to the desired site to effect release of the agent. The passage of the polymer carrier can be tracked by using imaging techniques such as, for example, magnetic resonance imaging of $^{19}F$. Optionally, the agent encapsulated in the polymer carrier can be tracked via imaging. For example, if the agent has particular characteristic such as luminescence or fluorescence, the agent itself can be tracked using an In Vivo Imaging System (IVIS) instrument, or if the agent is radioactive and emits gamma rays, it can be tracked using a Positron Emission Tomography (PET) imaging instrument

BRIEF DESCRIPTION OF THE DRAWINGS

FIG. 1 provides the amino acid sequence of an exemplary polymer carrier termed "$CE_2$-RGD-TFL". Trifluorinated leucines are indicated as Tfl and are bolded and underlined. The $CE_2$-RGD-TFL sequence is SEQ ID NO:18. Amino acids 1-12 represent N-terminal sequence, amino acids 13-32 represent Linker 1, amino acids 33-78 represent COMPcc sequence, amino acids 79-103 represent Linker 2, amino acids 104-155 represent elastin-like peptide domain and has the sequence $[(VPGVG)_2VPGFG(VPGVG)_2)]_2VP$ (SEQ ID NO:32), and amino acids 156-166 represent C-terminal sequence. The sequence VPGVG is SEQ ID NO:16, and the sequence VPGFG is SEQ ID NO:29. The sequence of the polymer carrier is 166 amino acids long. The molecular weight of the $CE_2$-RGD wild type (with none of the leucines being fluorinated) is 16147.27 and the molecular weight of $CE_2$-RGD-Tfl (where all the leucines are trifluorinated as 5,5,5-trifluoroleucine) is 16939.05.

DESCRIPTION OF THE DISCLOSURE

Figure 2:
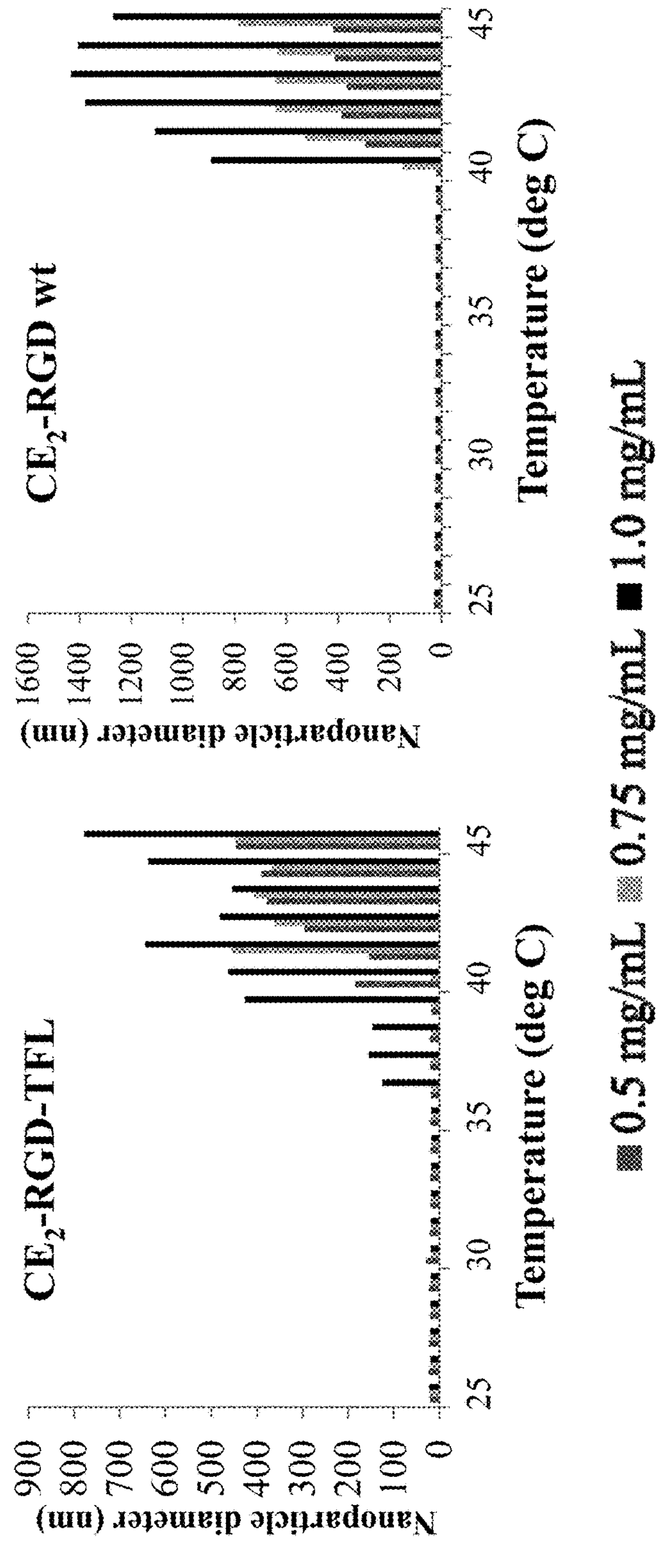
FIG. 2 is a representation of light scattering data for wild type ($CE_2$-RGD wt) and fluorinated ($CE_2$-RGD-TFL) polymer carrier.

The present disclosure provides protein polymer carriers, which are capable of providing dual functionalities of delivery and imaging, and are thermo-responsive. The disclosure also provides compositions comprising the polymer carriers and methods for making and using the same. The polymer carrier is a fluorinated protein block copolymer (FPBC). The FPBC can be used for delivery of therapeutic/diagnostic molecules and/or for imaging. The release of cargo can be effected by increasing the temperature. For example, the polymer carriers can be used for theranostic purposes as chemotherapeutic carriers and/or $^{19}$F MRI agents. The present protein polymers comprise a coiled-coil domain (C domain or COMPcc domain) and at least one elastin-like peptide domain (referred to herein as "E" or "E domain"), wherein one or more leucine residues in the protein polymer are fluorinated. An example of a fluorinated protein block copolymer, referred to herein as "$CE_2$-RGD-TFL", comprises two functional domains: 1) a COMPcc domain, flanked by two integrin targeting domains, and; 2) one or more sequential elastin-like peptide domains (Es). The coiled-coil domain is capable of encapsulating small molecules (such as small hydrophobic molecules) and the E domain can impart concentration dependent thermoresponsiveness. Depending on concentration, the protein will exhibit different thermal transition temperatures (Tt). For example, with increasing concentration, the transition temperature can decrease.

In the present FPBC, one or more leucine residues are fluorinated. The fluorinated leucines at each location may independently be monofluorinated, difluorinated, trifluorinated, tetrafluorinated, pentafluorinated or hexafluorinated. For example, one or more leucine residues are present as trifluoroleucine (Tfl). In one embodiment, all the leucine residues are fluorinated. For example, all the leucine residues are present as Tfls. The polymers of the present disclosure can perform dual functions of drug delivery and imaging.

The coiled-coil domain is the N-terminal coiled-coil of cartilage oligomeric matrix protein (COMP), and E represents elastin-like peptide repeat and comprises repeats of a pentapeptide sequence (VPGXG) (SEQ ID NO:15) where the X residue is valine but can be substituted with any amino acid other than proline, and "TFL" or "Tfl" indicates a fluorinated leucine.

The E domain can be represented as $E_n$, and the sequence of $E_n$ is $[(VPGXG)_2VPGXG(VPGXG)_2)]_n$ ($[(SEQ\ ID\ NO{:}15)_2(SEQ\ ID\ NO{:}15)(SEQ\ ID\ NO{:}\ 15)_2]_n$ or SEQ ID NO:30), wherein n is equal to or greater than 1. For example, the sequence can be $[(VPGVG)_2VPGFG(VPGVG)_2)]_n$ (SEQ ID NO:31). In this example, the VPGVG sequence corresponds to SEQ ID NO:16 and VPGFG sequence corresponds to SEQ ID NO:29, the E domain sequence can thus be represented as $[(SEQ\ ID\ NO{:}\ 16)_2(SEQ\ ID\ NO{:}29)(SEQ\ ID\ NO{:}\ 16)_2]_n$. From 1 to 3 amino acids (such as VP) or more may be present at the C-terminus end of the sequence. For n=1 (represented as $E_1$), the sequence contains 5 VPGXG repeats, and for n=2 (i.e., $E_2$), the sequence contains 10 VPGXG (SEQ ID NO:15) repeats and so on. In one embodiment, n is from 1 to 24 and all integer values therebetween. Thus, $E_5$ contains 25 VPGXG (SEQ ID NO:15) repeats and $E_{24}$ contains 120 VPGXG (SEQ ID NO:15) repeats. The "X" in the repeats can independently at each occurrence be any amino acid other the proline. For example, X at each occurrence can be V, or X at each occurrence can independently be V or F.

The cloned coiled-coil region of COMP (COMPcc) has the following sequence: GDLAPQMLRELQETNAALQDVRELLRQQVKEITFLKNTVMECDACGKLN (SEQ ID NO: 2). A cloned sequence of COMPcc useful for the present invention can have an N-terminal histidine tag for facile purification into a Pqe9 vector as follows:

```
                                        (SEQ ID NO: 1)
MRGSHHHHHHGSGDLAPQMLRELQETNAALQDVRELLRQQVKEITFLKNT
VMECDACGKLN.
```

The proteins may be expressed in a different vector that does not necessarily bear the N-terminal histidine tag. Depending upon whether the sequence bears a N-terminal histidine tag and which vector is used for cloning, the N-terminal sequence of the polymer carrier can vary.

The COMPcc homopolymer (and variants thereof) as well as block polymers of COMPcc can be purified using conventional methods. For the present use, variants of COMPcc may also be used. Examples of such variants are provided below. Amino acids from the wild type COMPcc without residual cloning amino acids is shown as SEQ ID NO:3, and variants or shown in SEQ ID NOs: 4-14. The mutated amino acids in variants of SEQ ID NOs: 4-14 are shown underlined and bolded.

wt: (SEQ ID NO: 3)
GDLAPQMLRELQETNAALQDVRELLRQQVKEITFLKNTVMECDACG

S: (SEQ ID NO: 4)
GDLAPQMLRELQETNAALQDVRELLRQQVKEITFLKNTVMESDASG

L37A: (SEQ ID NO: 5)
GDLAPQMLREAQETNAALQDVRELLRQQVKEITFLKNTVMESDASG

T40A: (SEQ ID NO: 6)
GDLAPQMLRELQEANAALQDVRELLRQQVKEITFLKNTVMESDASG

L44A: (SEQ ID NO: 7)
GDLAPQMLRELQETNAAAQDVRELLRQQVKEITFLKNTVMESDASG

L47A: (SEQ ID NO: 8)
GDLAPQMLRELQETNAALQDARELLRQQVKEITFLKNTVMESDASG

L51A: (SEQ ID NO: 9)
GDLAPQMLRELQETNAALQDVRELARQQVKEITFLKNTVMESDASG

Q54A: (SEQ ID NO: 10)
GDLAPQMLRELQETNAALQDVRELLRQAVKEITFLKNTVMESDASG

I58A: (SEQ ID NO: 11)
GDLAPQMLRELQETNAALQDVRELLRQQVKEATFLKNTVMESDASG

L61A: (SEQ ID NO: 12)
GDLAPQMLRELQETNAALQDVRELLRQQVKEITFAKNTVMESDASG

V65A: (SEQ ID NO 13)
GDLAPQMLRELQETNAALQDVRELLRQQVKEITFLKNTAMESDASG

S65A: (SEQ ID NO: 14)
GDLAPQMLRELQETNAALQDVRELLRQQVKEITFLKNTVMEADASG

The amino acids KLN (representing amino acids 59-61 in SEQ ID NO:1, and 47-49 in the SEQ ID No. 2) or corresponding amino acids in other sequences disclosed herein) represent residual amino acids from cloning. When a polymer protein is made using an expression vector, these amino acids can appear at the C-terminal end of the sequence as in SEQ ID NO:18.

In one embodiment, instead of or in addition to elastin-like domains, domains containing repeats from other proteins, such as keratin, silk, collagen and the like may be used.

The polymer carrier of the present disclosure can be expressed as comprising an amino acid sequence, which from the N- to the C-terminus, comprises the following blocks: COMPcc domain sequence, a linker, and one or more E domains. The linker between the COMPcc domain and an E domain is termed as Linker 2. The polymer can additionally comprise one or more of the following: an N-terminal sequence, a linker between the N-terminal sequence and the COMPcc sequence (termed as Linker 1), a C-terminal sequence.

The N-terminal sequence can be from 1 to 20 amino acids long and comprises methionine, and purification tags such as polyhistidine, and a dipeptide GS and may comprise residual amino acids from cloning.

The Linker 1 sequence can be from 1 to 20 amino acids and may comprise one or more of: integrin-binding sequence (such as, for example, RGD), AT repeats (such as, for examples, 2-8 repeats) and residual amino acids from cloning.

The COMPcc domain sequence can be SEQ ID NO: 3 or a variant thereof (such as SEQ ID Nos. 4-14) or a sequence that has at least 90 or 95% homology with any of these SEQ IDs.

Linker 2 sequence can be from 1 to 20 amino acids long. It is present between the COMPcc domain sequence and E domain sequence. It can comprise one or more of an integrin-binding sequence (such as, for example, RGD), AT repeats (such as, for example, from 2-8 repeats), and residual amino acids from cloning.

The elastin-like peptide or E domain sequence can be from 25 to 600 amino acids long, and can additionally have 1-3 residual amino acids such as VP. For example, it has the sequence $[(VPGXG)_2VPGXG(VPGXG)_2)]_n$(SEQ ID NO:30), wherein n can be from 1 to 24 and X can be any amino acid other than proline. The sequence VPGXG is SEQ ID NO:15.

The C-terminal sequence can be from 1 to 20 amino acids long. It comprises residual amino acids from cloning and can comprise one or more leucines.

The COMPcc sequence comprises leucine residues. For example, SEQ ID NOs. 3-14 have 7 leucine residues. One or more of the N-terminal sequence, Linker 1, Linker 2, and the C-terminal sequence may also comprise one or more leucines.

The molecular weight of the polymer carriers of the present disclosure can vary depending upon which blocks are present and the number of amino acids in the blocks. For example, the molecular weight of the polymer carriers can be from about 10,000 Da to about 75,000 Da. For example the molecular weight can be from 15,000 Da to about 60,000 Da.

In one example, the present polymer can comprise from the N- to the C-terminal: the N-terminal sequence, Linker 1 sequence, COMPcc domain sequence, Linker 2 sequence, and E domain sequence. In one example, the present polymer comprises from the N- to the C-terminal: N-terminal sequence, Linker 1 sequence, COMPcc domain sequence, Linker 2 sequence, E domain sequence, and C-terminal sequence.

Figure 10:
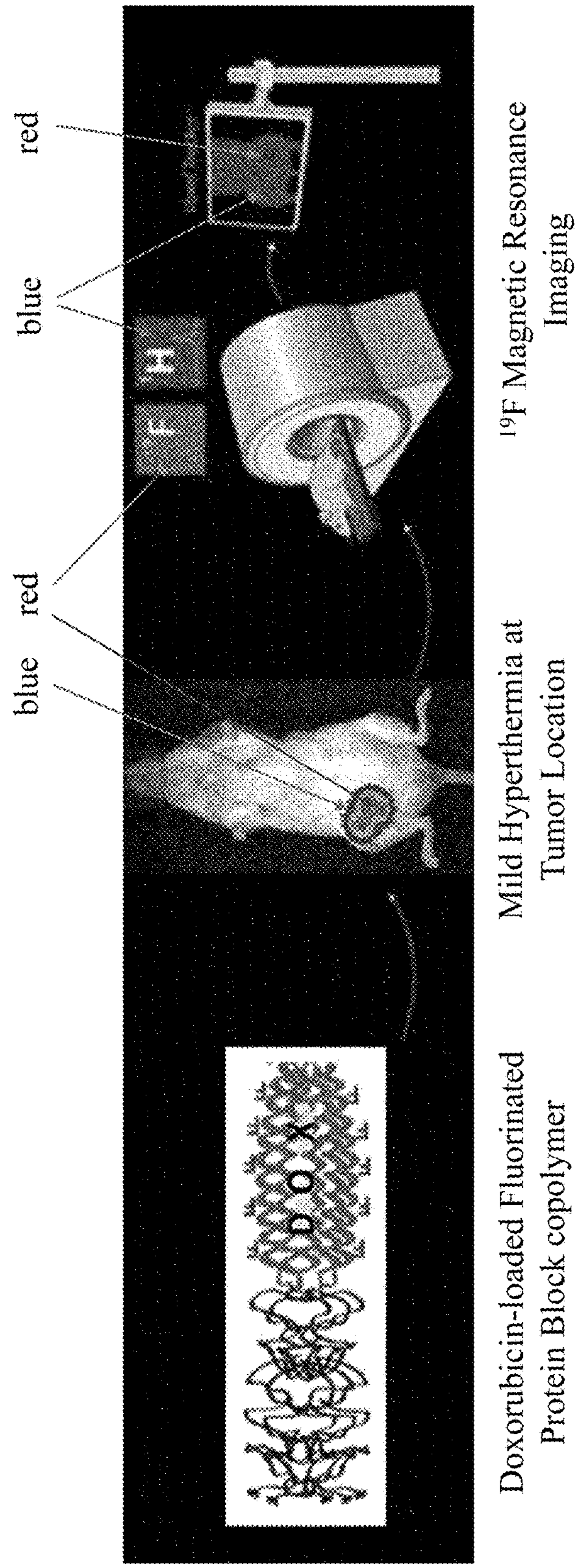
FIG. 10 is a model for an application for the fluorinated ($CE_2$-RGD-TFL) polymer carrier illustrating the administration of the doxorubicin loaded $CE_2$-RGD-TFL, application of heat locally, and magnetic resonance imaging to confirm homing of the drug carrying polymer.

The FPBC can be used for targeted, stimuli-driven small molecule (such as, for example, chemotherapeutic agents) delivery and/or $^{19}F$ magnetic resonance imaging of the drug delivery vehicle. For example, FPBCs such as $CE_2$-RGD-TFL may: 1) actively target cells (such as any type of cancer cells, including, for example, breast cancer cells) and trigger the release of a chemotherapeutic payload in a stimuli-responsive fashion through localized hyperthermia induction in which the hyperthermic temperatures (such as 38° C. to 42° C. and all temperatures therebetween) can enable release of cargo; 2) exploit the cumulative effect of longer retention of the payload at the tumor site via enhanced permeation retention (EPR) in combination with hyperthermia-driven extravasation of a drug by FPBCs such as $CE_2$-RGD-TFL to enhance anti-tumor efficacy in the heated region; and 3) its fate tracked via $^{19}F$ NMR or MRI and effective activity assessed via T2-relaxometry or similar T2 pulse sequences (Zero Echo Time MRI or Ultrashort Echo Time MR) as governed by the thermo-responsive protein block polymer enabling confirmation of drug carrier location and drug release (See FIG. 10). Hyperthermia may be achieved by any means that can raise the temperature of the desired location. For example, hyperthermia can be achieved by applying a heating pad to the outside of the body near the tumor site or by focused ultrasound.

The C domain is derived from the N-terminal coiled-coil of cartilage oligomeric matrix protein, which can self-assemble into a pentameric alpha helical coiled-coil and also bears a hydrophobic pore (7.3 nm long, 0.2-0.6 nm diameter) that can entrap small molecules of therapeutic value such as doxorubicin, vitamin D, all-trans-retinol and curcumin (Gunasekar et al., Biochemistry 2009, 48, 8559). The present polymer carriers can be used for all of these small molecules as well as all other small molecules, such as, for example, retinoid antagonists/inverse agonists, taxols, peptides, other anticancer and antiarthritis drugs and the like, and hydrophilic agents. Studies have shown that mutations at the internal aliphatic residues within the pore are vital to small molecule binding with some mutations actually enabling greater binding (Gunasekar et al., Biochemistry 2009, 48:8559). The E domain refers to an elastin-like peptide repeat and it imparts thermoresponsiveness upon the protein whereby there is a transition temperature ($T_t$) at which the domain shifts from a disordered structure to beta-spiral structure. The E domain comprises repeats of pentapeptide sequence (VPGXG) (SEQ ID NO:15) where the X residue is valine but can be substituted with any amino acid to alter the thermoresponsiveness of the domain. It was found that the number of E domain repeats impacted the transition temperature (Dai et al., Biomacromolecules 2011, 12:4240).

The $CE_2$-RGD-TFL protein has two integrin-binding tripeptide (RGD) guest sequences flanking the C domain such that in one embodiment, the protein can be described as comprising from N- to C-terminal: integrin binding tripeptide, COMPcc domain, integrin binding tripeptide, and E domain. For example, the protein can comprise from N- to C-terminus: RGD, COMPcc domain, RGD, and E domain. In one embodiment, the FPBC has the sequence shown in FIG. 1. One or more amino acids (such as AT rich sequences or cloning residual sequences) may be present between adjacent RGD and COMPcc domain, and between COMPcc and E domain. In addition, the protein may have a polyhistidine tag. For example, the protein may comprise: from the N- to the C-terminus: [MXn], [HHHHHH] (SEQ ID NO:17), residual cloning sequence, RGD, AT rich sequence, COMPcc domain, residual cloning sequence, AT rich sequence, residual cloning sequence, E domain, residual cloning sequence, where X is any amino acid and n is a number from 1 to 20 amino acids. Unlike the para-fluorophenylalanine (pFF) variants of $CE_5$, $E_5C$, and $E_5CE_5$, the present $CE_2$-RGD-TFL is fluorinated with 5,5,5-trifluoroleucine (TFL). This can be accomplished, for example by way of residue-specific incorporation via a leucine auxotrophic *E. coli* strain (Lam-1000). Incorporation occurs at 11 native leucine sites in one example of the $CE_2$-RGD construct. Seven of these sites are present in the COMPcc domain at the internal hydrophobic pore of the larger coiled-coil structure while the remaining 4 reside elsewhere in the polymer.

The polymer protein can be represented, in one example, as comprising from N- to C-terminus: N-terminal sequence, Linker 1, COMPcc domain, Linker 2, E domain, and C-terminal sequence. The N-terminal sequence comprises poly histidine tag, Linker 1 comprises integrin-binding tripeptide, a leucine residue that can be fluorinated as Tfl, and AT repeats, the COMPcc domain is the coiled-coil region of COMP, the Linker 2 comprises an integrin-binding tripeptide and AT repeats, the E domain comprises repeats of VPGVG (SEQ ID NO:16) and may contain extra VP amino acids at the ends, the C-terminal sequence comprises one or more leucines that can be fluorinated as Tfls.

An example of a sequence of the polymer protein is

```
                                        (SEQ ID NO: 18)
MRGSHHIIHHHGSACELAARGDATATATATAACGDLAPQMLRELQETNAAL

QDVRELLRQQVKEITFLKNTVMESDASGLQAARGDATATATATAVDKPIAA

SAVPGVGVPGVGVPGFGVPGVGVPGVGVPGVGVPGVGVPGFGVPGVGVPGV

GVPLEGSGTGAKLN.
```

In this sequence, the first 12 amino acids represent the N-terminal sequence, which comprises a histidine tag, the next 20 amino acids represent Linker 1 and comprise a leucine that can be fluorinated as Tfl, a RGD sequence, and an AT rich sequence; the next 46 amino acids represent the COMPcc domain; the next 25 amino acids represent Linker 2, which comprises an RGD sequence and an AT rich sequence; the next 52 amino acids represent the E domain; and the next 11 amino acids represent the C-terminal linker, which comprises two leucine residues which are replaced by Tfl. Thus, in the sequence above, the various elements are:

```
                                        (SEQ ID NO: 19)
MRGSHREIHHEGS - N-terminal sequence

                                        (SEQ ID NO: 28)
ACELAARGDATATATATAAC - Linker 1

                                        (SEQ ID NO: 20)
GDLAPQMLRELQETNAALQDVRELLRQQVKEITFLKNTVMESDASG -
COMPcc domain

                                        (SEQ ID NO: 21)
LQAARGDATATATATAVDKPIAASA - Linker 2

                                         SEQ ID NO: 22)
VPGVGVPGVGVPGFGVPGVGVPGVGVPGVGVPGVGVPGFGVPGVGVPGVG
VP - E domain

                                        (SEQ ID NO: 23)
LEGSGTGAKLN - C-terminal sequence
```

The RGD peptides were introduced by site-directed mutagenesis whereby RGD was included within the AT-rich linker sites. These RGD sites were mutated into the protein for the purpose of cellular targeting to cancer cells, such as MCF-7 and MDA-MB-231, which overexpress integrins. The introduction of these RGD guest peptides has a stabilizing effect on the protein as evidenced by an increase in the transition temperature (45.4° C. to 47.4° C.) compared to the parent $CE_2$-RGD construct (FIG. 1) In one embodiment, instead of or in addition to the integrin-binding motif RGD, other targeting motifs could be used—such as Her2/new, folate receptor, CD44 and the like.

FPBCs, such as $CE_2$-RGD-TFL are advantageous theranostic agent in that the entirety of the material, aside from the non-natural amino acid, is derived from biological material making it a suitably biocompatible drug delivery candidate. In terms of $^{19}F$ MRI contrast agents alone, $CE_2$-RGD-TFL aligns with the newer class of "smart" agents but takes one step forward in that the stimulus is an externally applied heat that triggers a structural change in the protein, which imparts the imaging function of the T2-nano-thermometer. Furthermore, $CE_2$-RGD-TFL is a drug carrier that is considered to release the encapsulated drug upon reaching the protein transition temperature.

The cargo that may be encapsulated can be hydrophobic and/or hydrophilic molecules. In one embodiment, the cargo comprises small hydrophobic molecules. Examples include, but are not limited to, doxorubicin, vitamin D, all-trans-retinol and curcumin.

In one aspect this disclosure provides nucleic acid sequences that are capable of encoding polymer carriers or fusion proteins comprising the polymer carriers. The recombinant gene may be expressed and the polypeptide purified utilizing any number of methods. In one embodiment, the nucleic acid encoding the carrier can be fused with a receptor-binding domain of a ligand.

The proteins of the present disclosure include functionally equivalent molecules in which amino acid residues are substituted for residues within the sequence resulting in a silent or conservative change. For example, the functionally equivalent molecules may have a sequence that is at least 90 or 95% identical. One or more amino acid residues within the sequence can be substituted by another amino acid of a similar polarity that acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof, which exhibit the same or similar biological activity and derivatives, which are differentially modified during or after translation, for example, by glycosylation, proteolytic cleavage, and linkage to other ligands.

For expression of the proteins, the nucleic acid sequences encoding the carrier protein may be inserted into a recombinant vector, which may be plasmids, viruses or any other vehicle known in the art that has been manipulated by the insertion or incorporation of the nucleic acid sequences encoding the chimeric peptides of the invention. The recombinant vector typically contains an origin of replication, a promoter, as well as specific genes that allow phenotypic selection of the transformed cells. Vectors suitable for use in the present invention include but are not limited to the T7-based expression vector for expression in bacteria or viral vectors for expression in mammalian cells, baculovirus-derived vectors for expression in insect cells, and cauliflower mosaic virus (CaMV), tobacco mosaic virus (TMV), and other vectors.

Depending on the vector utilized, any of a number of suitable transcription and translation elements, including constitutive and inducible promoters, transcription enhancer elements, transcription terminators, etcetera, may be used in the expression vector. Such construction of expression vectors and the expression of genes in transfected cells can involve the use of molecular cloning techniques (for example, in vitro recombinant DNA techniques, synthetic techniques, and in vivo recombination/genetic recombination), bacterial systems for the expression of vectors, yeast systems with constitutive or inducible promoters, insect systems, prokaryotic and eukaryotic systems using transfection or co-transfections of DNA vectors, transgenic animals using for example viral infection, and embryonic stem cells. Methods and procedures for using and applying such vectors are widespread in publications and are known or easily obtainable by persons of ordinary skill in the art.

The carrier (along with the small molecule) of the present invention may be formulated with conventional pharmaceutical carriers. The carrier may be in conventional pharmaceutical administration forms such as powders, solutions, suspensions, dispersions, etcetera; however, solutions, suspensions, and dispersions in physiologically acceptable carrier media. For example, such materials include emulsifiers, fatty acid esters, gelling agents, stabilizers, antioxidants, osmolality adjusting agents, buffers, preservatives, antimicrobial agents, and pH adjusting agents. Further, delivery mechanisms include parenteral administration (injection or infusion directly). The compositions according to the invention may therefore be formulated for administration using physiologically acceptable carriers or excipients in a manner fully within the skill level of the art.

The FPBCs may be purified by any technique that allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the FPBCs, any number of purification methods may be used, including but not limited to conventional ion exchange chromatography, affinity chromatography, different sugar chromatography, hydrophobic interaction chromatography, reverse phase chromatography, or gel filtration.

In addition, covalent conjugation to other biocompatible and biodegradable polymers or small molecules such as PEG, PLA, PLGA, or fatty acids can be carried out.

It is contemplated that embodiments of this invention can have an array of applications. In the field of nutrition, the present carrier may provide a matrix for stabilization in vitamins and nutritional supplements, allowing for extended shelf life and efficacy. In the field of pharmaceuticals, the carrier can help with solubilizing as well as stabilizing drugs and providing a delivery vehicle, and through mutation of the sequence to tune the delivery kinetics of drugs. In regenerative medicine, the carrier may be fused with other biopolymers to produce scaffold for tissue engineering.

Applications of this invention include but are not limited to drug delivery and/or $^{19}F$ magnetic resonance imaging. The applications of this technology are wide ranging. For example, the promiscuity of the C domain towards hydrophobic drug molecules provides a wide breadth of diseases to treat. Alternatively, or additionally, the C domain can encapsulate hydrophilic molecules. The integrin-binding domain (RGD) may be substituted for targeting other disease-state biomarkers. In this sense, one can use the fluorinated protein block copolymer as a platform theranostic agent for simultaneous stimulus-trigged $^{19}F$ magnetic resonance imaging and/or magnetic resonance spectroscopy and targeted drug release.

The fluorinated protein block copolymers are magnetic resonance detectible tracers or contrast agents. The copolymers can be used in imaging methods and imaging devices known in the art. The copolymers can be imaged (e.g., the location of the copolymers in an individual monitored) using, for example, $^{19}F$ magnetic resonance imaging or magnetic resonance spectroscopy. The copolymer can be imaged in vivo (e.g., imaging after administration of the copolymer to an individual) or in vitro (e.g., imaging cells obtained from an individual after administration of the copolymer to an individual). Multimodal imaging methods (e.g., asynchronous or synchronous methods) and/or quantitative imaging methods may be used.

In one embodiment, the present disclosure provides a method for delivery and/or imaging comprising: a) administering to an individual a composition comprising the polymer carriers as described herein; b) tracking the transport of the composition via MRI imaging; c) when the composition reaches a desired location, increasing the temperature to 38 to 42° C. thereby releasing at least a portion of the agent from the polymer carrier at the desired location. For in vitro use, heat may be applied via placing in an incubator. For in vivo use, temperature may be increased via heating pad or via focused ultrasound The present disclosure demonstrates that incorporation of TFL in $CE_2$-RGD yields a drug carrier nanoparticle that can undergo temperature dependent structural changes measured by an increase in R2 values, which indicates that $CE_2$-RGD-TFL can be used as a T2-weighted MRI contrast agent. Also, fluorination imparts both greater thermoresponsiveness and greater loading of agents (such as doxorubicin), which provides further value to $CE_2$-RGD-TFL as a theranostic agent.

The present polymer carriers are drug delivery vehicles that can: a) actively target tumor types; b) exhibit triggered release of a drug at the tumor site; and c) possesses the ability to be anatomically imaged for confirmation of vehicle localization at or near the tumor. Use of these delivery vehicles can potentially limit off-target effects of therapeutic agents (such as doxorubicin) and maximize their delivery to the desired site (such as tumor).

The following example is provided to further illustrate the invention and is not intended to be restrictive in any way.

Example

This example provides characterization of the protein shown in FIG. 1.

Methods:

Site-Directed Mutagenesis $CE_2$-RGD is derived from the $CE_2$ parent construct that was previously generated and thoroughly characterized (Dai et al., Biomacromolecules 2011, 12, 4240). The two RGD mutations located at sites flanking the C domain were introduced by site-directed mutagenesis in the PQE30/$CE_2$ plasmid. Mutant constructs were generated by a polymerase chain reaction (PCR) using high fidelity PFU Taq polymerase (Thermo Fisher Scientific) and the following primers from MWG Operon:

```
RGDlink1fwd                         (SEQ ID NO: 24)
5'-GAGCTCGCTGCTCGTGGCGACGCCACTGCTACG-3'

RGDlink1rev                         (SEQ ID NO: 25)
5'-CGTAGCAGTGGCGTCGCCACGAGCAGCGAGCTC-3'

RGDlink2fwd                         (SEQ ID NO: 26)
5'-CTGCAGGCTGCCCGTGGCGACGCTACTGCAACC-3'

RGDlink2rev                         (SEQ ID NO: 27)
5'-GGTTGCAGTAGCGTCGCCACGGGCAGCCTGCAG-3'
```

Following PCR, the methylated parent strand of the PQE30 plasmid was digested for 3 hours at 37° C. with DpnI enzyme (Thermo Fisher Scientific) theoretically resulting in a homogeneous plasmid population consisted of only mutant RGD-bearing plasmid constructs. The resultant mutant constructs were transformed into chemically competent XL1-Blue *E. coli* cells and permitted to grow on tryptic soy agar (TSA) plates for approximately 16 hours at 37° C. under ampicillin (200 μg/mL) antibiotic selection control (Thermo Fisher Scientific). Upon confirmation of colony growth, single colonies were selected for growth in Luria broth (Thermo Fisher Scientific) liquid cultures for approximately 20 hours at 37° C. The DNA was extracted from the cells and purified (Zymogen). The resulting purified plasmid (PQE30/$CE_2$-RGD) was sent out for sequencing (Eurofins) to confirm successful mutation of nine nucleotides that would produce the RGD peptide sequence in place of a TAT peptide sequence.

PQE30/$CE_2$-RGD plasmid was transformed into electrocompetent leucine auxotrophic lam-1000 cells (Panchenko et al. *Biotechnology and Bioengineering* 2006, 94, 921) and permitted to grow on TSA plates for approximately 12 hours at 37° C. under both kanamycin (35 μg/mL) and ampicillin (200 μg/mL) antibiotic selection control (Thermo Fisher Scientific). Upon confirmation of colony growth, single colonies were selected for growth in starter cultures (3 mL) of minimal media M9 (0.5 M $Na_2HPO_4$, 0.22 M $KH_2PO_4$, 0.08 M NaCl, 0.18 M $NH_4Cl$) in the presence of kanamycin (35 μg/mL), ampicillin (200 μg/mL), vitamin B (35 μg/mL), $MgSO_4$ (100 mM), $CaCl_2$ (0.1 mM), 20 amino acids (40 μg/mL) for approximately 16 hours at 37° C. and 350 rpm. The starter cultures were then transferred to a large scale expression flask (200 mL) containing the aforementioned M9 media and associated chemicals in the exact concentrations. The large scale cultures were grown at 37° C. and 300 rpm until the optical density at 600 nm reached 0.8-1.0. At this point, the cells were pelleted by centrifugation at 4000 rpm for 15 minutes at 4° C., and washed three times with ice cold 0.9% NaCl (Thermo Fisher Scientific) prepared in deionized $H_2O$. After the final centrifugation, the pellet was re-suspended in the aforementioned M9 media with 19 amino acids, minus leucine (40 μg/mL) all other associated chemicals. The re-suspended cell mixture was permitted to grow for an additional 15 minutes at 37° C. and 300 rpm to exhaust any additional leucine. Following this growth period, 5,5,5-trifluoro-L-leucine (TFL) (555 μg/mL) and Isopropyl β-D-1-thiogalactopyranoside (IPTG) (200 μg/mL) (Thermo Fisher Scientific) were added. This enabled expression and residue specific incorporation of TFL. After 3 hours of protein expression at 37° C. and 300 rpm, the cells were pelleted by centrifugation at 4000 rpm for 15 minutes at 4° C. The cell pellets were store at −80° C. until purification.

Cell pellets were permitted to thaw at 4° C. for 30 minutes and then resuspended in lysis buffer (6 M urea, 50 mM $Na_2HPO_4$, 10 mM imidazole, pH 8.0) and lysed by 4 freeze-thaw cycles between 80° C. and room temperature and also by ultrasonic probe sonication (Q500 sonicator, amplitude 80%, pulse 5 seconds on and 15 seconds off, for a total sonication time of 1:30 min). The cell lysate was centrifuged at 13,500 rpm for 1 hour and 30 minutes at 4° C. The supernatant was then passed through a HiTrap IMAC FF (5 mL, GE life sciences), which was charged with 100 mM $CoCl_2$. The protein of interest was eluted by increasing elution buffer (6 M urea, 50 mM $Na_2HPO_4$, 1 M imidazole, pH 8.0) concentration from 2% and 100% v/v. Fractions of 5 mL were collected and ran on 12% sodium dodecyl sulfate polyacrylamide gel electrophoresis (SDS-PAGE) to confirm purity. Pure protein was then dialyzed in snakeskin tubing, 3.5 K molecular weight cut off (MWCO) (Thermo Fisher Scientific) across 4 buckets (3 Liters each) of 50 mM $Na_2HPO_4$, 0.5 M NaCl, pH 8.0 at 4° C. Following dialysis, the protein concentration was determined by a bicinchoninic acid (BCA) assay (Pierce Thermo Fisher Scientific).

Circular dichroism (CD) spectroscopy was used to confirm the secondary structure. This was accomplished using a Jasco J-815 CD spectrometer with a PTC-423 S single position Peltier temperature control system. For CD experiments assessing the protein structure alone, protein concentrations were kept constant at 0.200 mg/mL in of 50 mM $Na_2HPO_4$, 0.5 M NaCl, pH 8.0. The wavelength spectrum was measured over the range of 200-300 nm with a bandwidth (step size) of 1 nm. The scanning mode was continuous at 20 nm/minute. All wavelength CD runs were conducted at 4° C.

In terms of calculations for CD analysis, molar residue ellipticity ($\theta_{MRE}$) was calculated from ellipticity (θ) using the following equation:

(1) $\theta_{MRE}=\theta/(10*\text{Protein Conc.}*\text{Path Length}*\text{Length of Sequence})$ [4]

A mixture of 100 μM free doxorubicin (DOX) (see the extraction method below) and either $CE_2$-RGD or $CE_2$-RGD-TFL and standards (100 μM, 75 μM, 50 μM, 25 μM, 10 μM, 5 μM and 0 μM) were incubated at 4° C. for 2 hours in the dark. After this incubation period, the mixtures were subjected to G-25 Sephadex (Sigma-Aldrich) gel filtration chromatography with fifteen elutions of 50 mM $Na_2HPO_4$, 0.5 M NaCl, pH 8.0 at room temperature. The eluted fractions were subjected to absorbance readings ranging from 420-600 nm (Molecular Devices Spectramax M2). The eluted fraction with highest absorbance reading at 485 nm was incorporated in the standard curve trendline equation to determine the total concentration of DOX bound to the protein. That protein sample was also subjected to the BCA assay enhanced protocol to determine the total protein concentration.

Extraction of DOX from a doxorubicin-HCl (DOX-HCl) was required to achieve free hydrophobic doxorubicin for pore encapsulation. This was accomplished by mixing a solution of DOX-HCl (862 μM) and triethylamine (3 moles equivalent, 2.59 mM) and stirring this solution for 7 hours at room temperature. Chloroform (20 mL) was then added to the DOX-HCl/triethylamine mixture and stirred overnight (16 hours) at room temperature. Successive chloroform extractions (20 mL) containing free DOX were removed from the organic phase of a separatory funnel. After ~120 mL of free DOX/chloroform was removed, the mixture was subjected to rotary evaporation (Labconco Rotary Evaporator). The residual volume was evaporated under nitrogen gas and finally dissolved in 1 mL DMSO. The final concentration of free DOX was determined by generating a standard curve from absorbance of DOX-HCl from 420-600 nm and incorporating the free DOX into the trendline equation. The absorbance measurement for free DOX concentration determination was taken at 485 nm.

$CE_2$-RGD or $CE_2$-RGD-TFL, of varying concentrations, in 50 mM $Na_2HPO_4$, 0.5 M NaCl, pH 8.0 were loaded into a type 21 quartz cuvette that had a 10 mm path length (BuckScience, Los Angeles, Calif.). Proteins were characterized for their temperature transition ($T_t$) behavior at a wavelength of 320 nm using a UV-Vis Cary-50 (Varian Inc., Cary, N.C.) equipped with a TC125 temperature regulator (Quantum Northwest, Liberty Lake, Wash.). Samples were heated at a rate of 1° C./minute from 15° C. to 85° C. The $T_t$ was determined by taking the first derivative of the normalized absorbance (320 nm) as a function of temperature.

Dynamic light scattering (DLS) measurements were performed on a Zetasizer Nano Series model Nano ZS90 in a type 21 quartz cuvette with the applied settings: material protein (refractive index 1.450), absorption 0.001, dispersant PBS with a viscosity of 1.0200 cP and refractive index of 1.335. Measurements were taken in triplicates, conducting 10 runs for each measurement, with a delay time of 2 seconds. Approximately, 1.0 mL of 0.5, 0.75 or 1.0 mg/mL $CE_2$-RGD-TFL or $CE_2$-RGD in 50 mM $Na_2HPO_4$, 0.5 M NaCl, pH 8.0 was then added to the cell.

Nuclear Magnetic Resonance (NMR) experiments were carried out on a 500 MHz (11.7 Tesla) Bruker Avance II instrument equipped with a 5 mm room-temperature BBFO SMART probe and Topspin 3.2 software. For variable temperature (27° C., 37° C. and 42° C.) $^{19}F/^{1}H$ decoupling experiments, $CE_2$-RGD-TFL (1.2 mg/mL) was subjected to 15000 scans with a sweep width of 76.62 ppm, acquisition time of 0.4547 seconds, relaxation time of 1.0 second, pulse length of 15 μseconds and referenced with 0.01% para-fluorophenylalanine. Both the inversion recovery and Car-Purcell-Meiboom-Gill (CPMG) $^{19}F$ NMR experiments were performed on $CE_2$-RGD-TFL (0.5 mg/mL, 0.6 mg/mL, 0.75 mg/mL, 0.9 mg/mL) at varying temperatures (22° C., 27° C., 32° C., 37° C.). The relaxation times ($T_1$ and $T_2$) were determined by using Topspin 3.2 software.

Magnetic Resonance imaging (MRI) experiments were carried using a 2D Gradient echo (GE) MRI. For GE experiments, a solution of approximately 5 mg/mL $CE_2$-RGD-TFL (total volume ~500 μL) (FIG. 8) and a negative control volume of water were placed in separate 5 mm NMR tubes and subjected to scanning in a home-made coil. A broadband tuning and matching solenoid coil was developed to cover both Larmor frequencies of $^{1}H$ proton (300.16 MHz) and $^{19}F$ (282.4 MHz) at 7T. The solenoid coil was made from silver plated copped wire wrapped tightly around a plastic holder that can hold up to 2 glass tubes (OD 6 mm). The coil was first tuned and matched for $^{1}H$ scan that provide more signal and can be used as reference for $^{19}F$ scan. A 2D Gradient Echo (GE) sequence was used with 50 mm slice thickness (covering the whole length of the tube) and 300 μm in-plane (matrix size 64×64, TE 2.2 ms, TR 30 ms, scanning time 2 seconds). The coil was then tuned to $^{19}F$ frequency and scanned using the same sequence with lower resolution (600 μm in-plane, matrix size 32×32, scanning time 14 hours Transmission electron microscopy (TEM) experiments were undertaken to visualize and confirm particle sizes. The $CE_2$-RGD-TFL (0.5 mg/mL) was heated to 20° C. or 50° C. for 1.5 hours followed by application of the protein onto copper square mesh TEM grids and 1% uranyl acetate negative staining. The TEM grids were imaged using a FEI Titan Halo 300 kV electron microscope.

Figure 3:
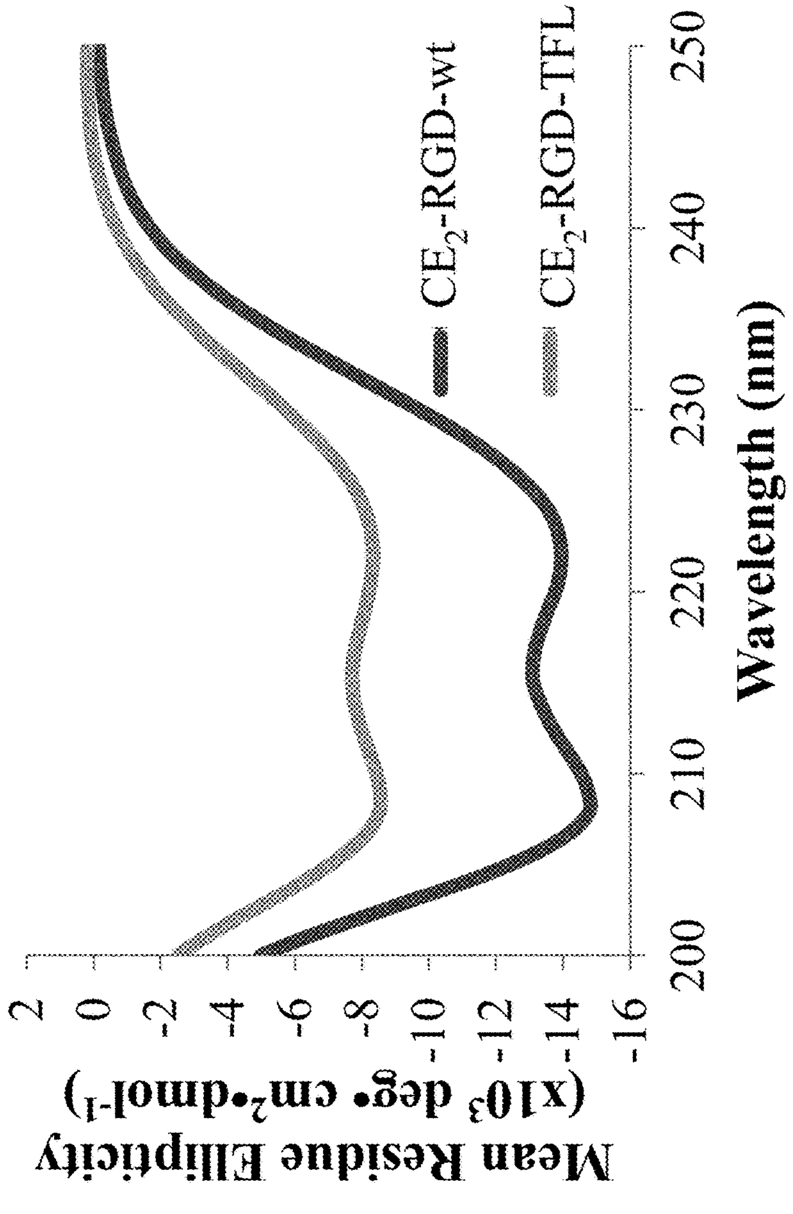
FIG. 3 is a representation of circular dichroism spectra for wild type ($CE_2$-RGD wt) and fluorinated ($CE_2$-RGD-TFL) polymer carrier.
Figure 4:
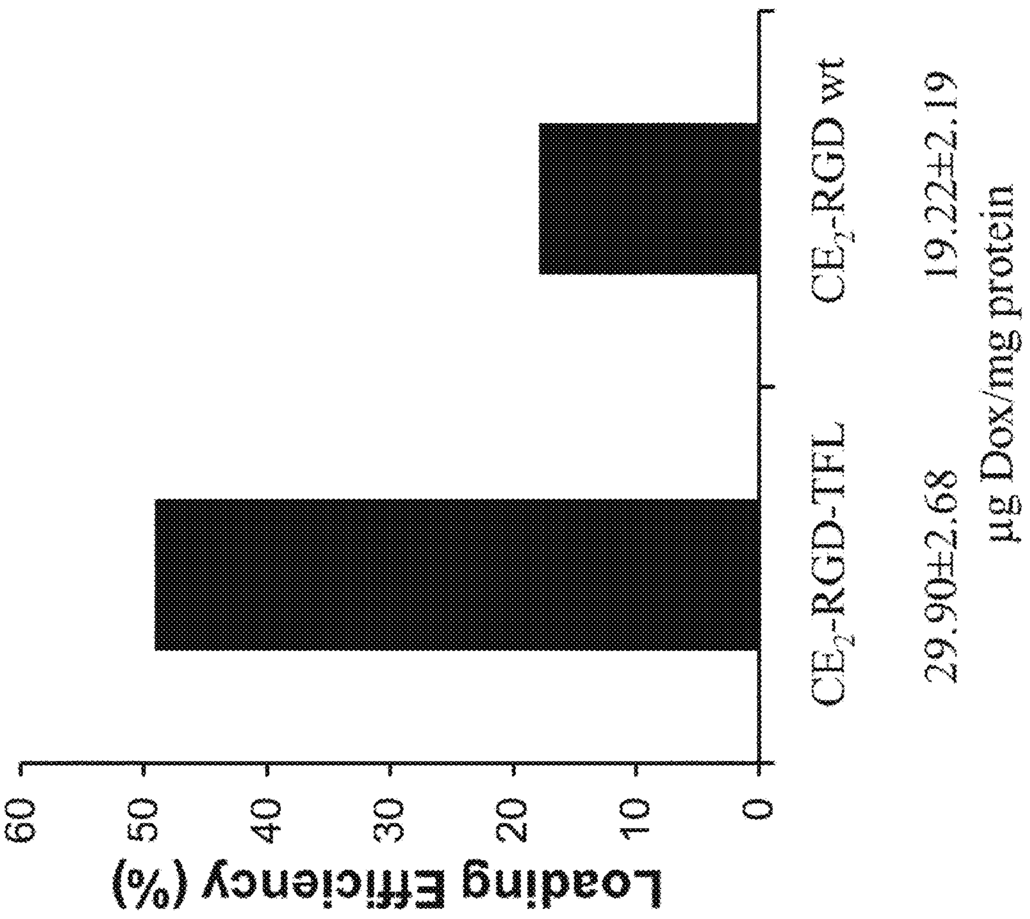
FIG. 4 is a representation of doxorubicin loading efficiency for wild type ($CE_2$-RGD wt) and fluorinated ($CE_2$-RGD-TFL) polymer carrier.
Figure 5:
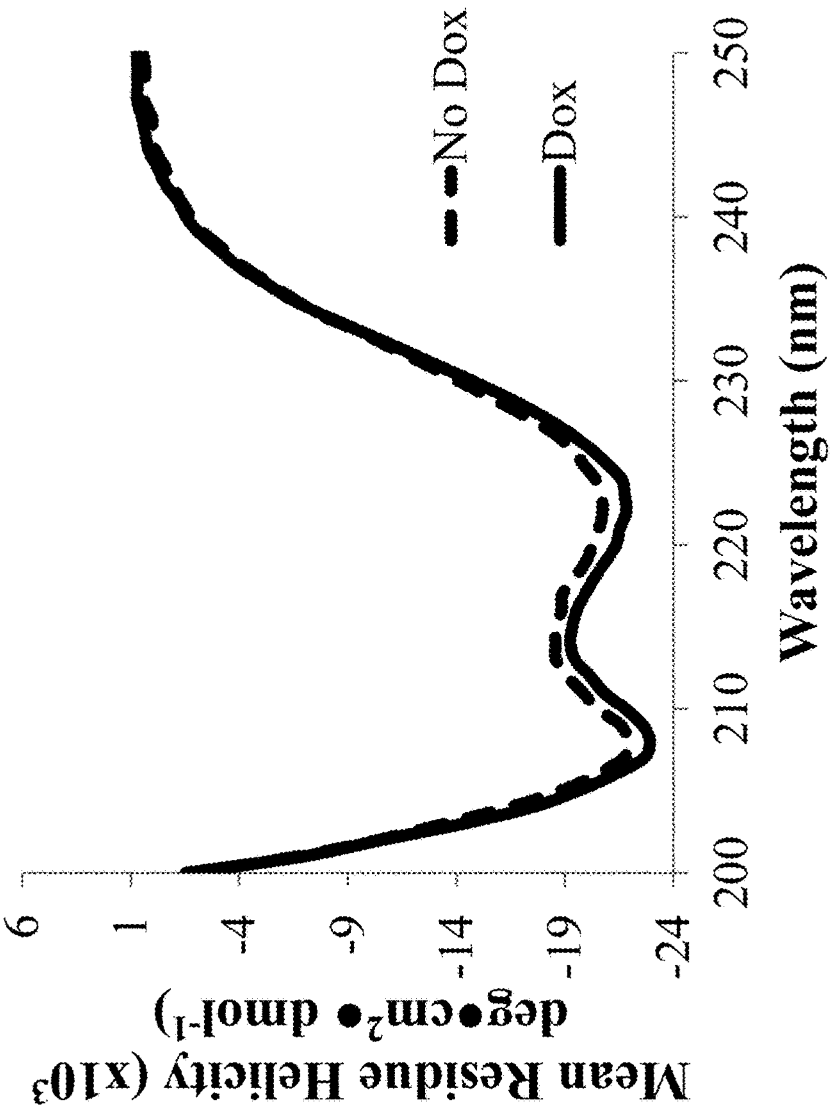
FIG. 5 is a representation of circular dichroism spectra for fluorinated ($CE_2$-RGD-TFL) polymer carrier in the presence and absence of doxorubicin.
Figure 6:
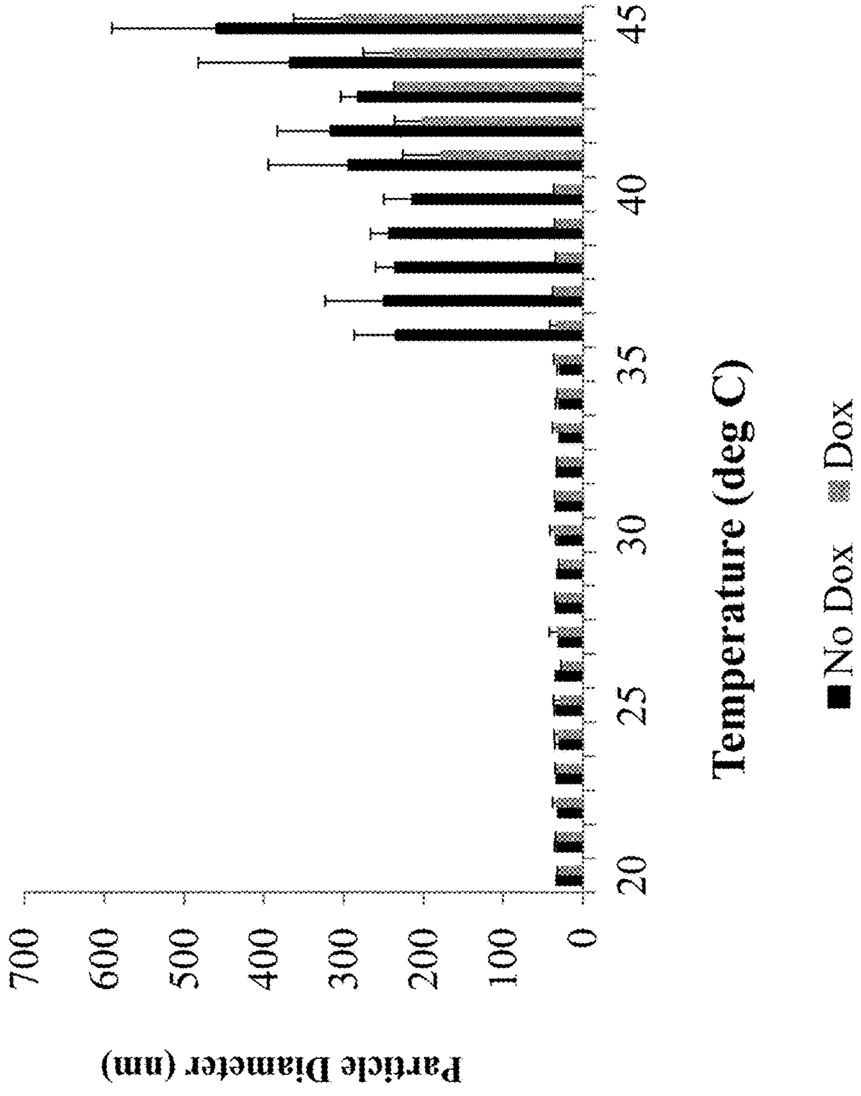
FIG. 6 is a representation of dynamic light scattering data for fluorinated ($CE_2$-RGD-TFL) polymer carrier in the presence and absence of doxorubicin as a function of temperature.
Figure 11:
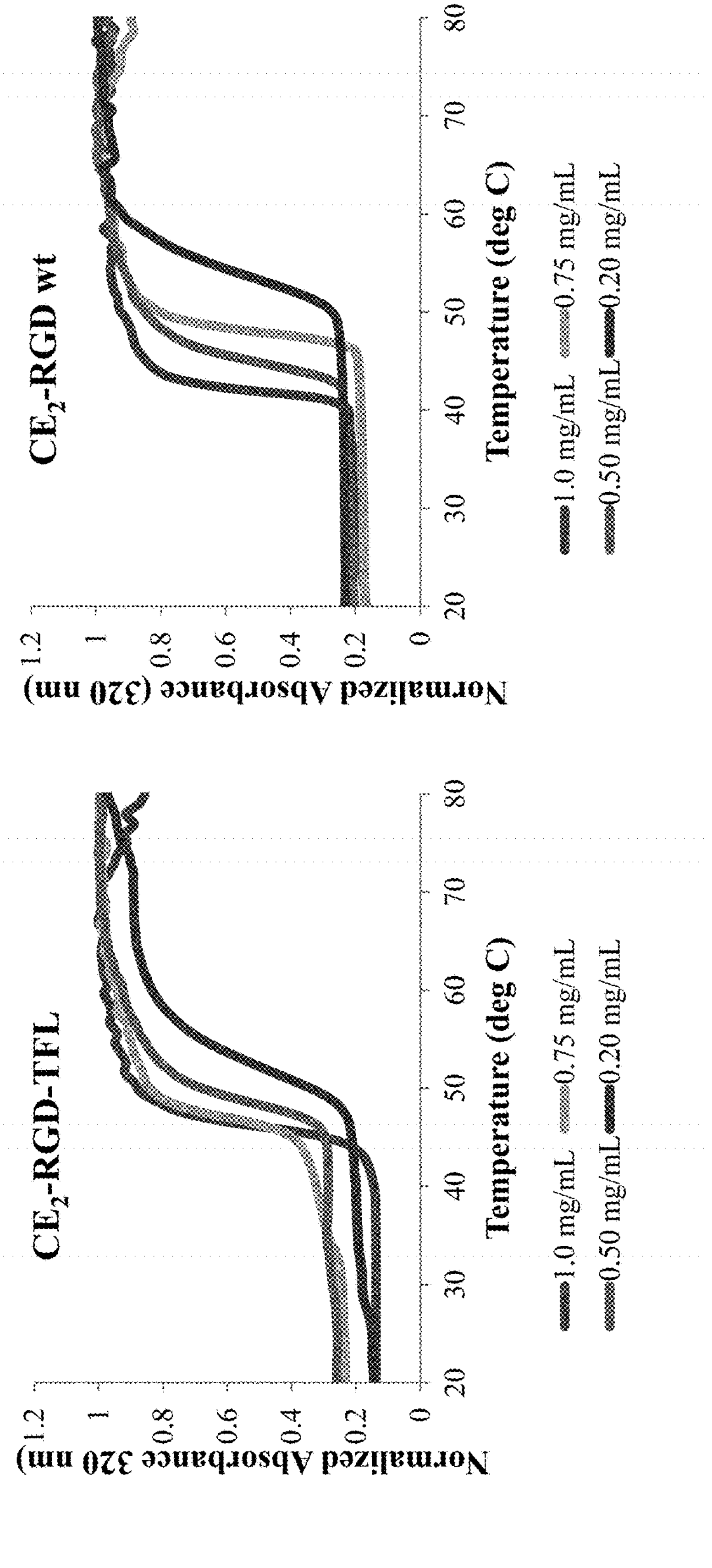
FIG. 11 is a representation of UV-visual spectroscopy showing concentration dependent transition temperatures for wild type ($CE_2$-RGD wt) and fluorinated ($CE_2$-RGD-TFL) polymer carriers.

Regarding the transition temperature, TFL incorporation imparted a stabilizing effect on the protein (Table 1, FIG. 2). The increased resistance to temperature-driven coacervation is likely due to the hydrophobic nature of fluorine. Circular dichroism secondary structure analysis of both $CE_2$-RGD-TFL and $CE_2$-RGD reveal less structure for the fluorinated variant (FIG. 3). The transition temperatures for both protein fall within the physiological range for mild hyperthermic drug delivery (38° C. to 42° C.) (See FIG. 11). An additional benefit of the fluorinated variant is that it encapsulates 49.1% of available doxorubicin upon saturation while the wild-type $CE_2$-RGD encapsulates 17.8%. This permits 19.22±2.19 μg doxorubicin loading per milligram of wild-type $CE_2$-RGD and 29.90±2.68 doxorubicin loading per milligram of $CE_2$-RGD-TFL (FIG. 4). Upon loading of doxorubicin into $CE_2$-RGD-TFL, there is an increase in secondary structure as exhibited in the circular dichroism spectra (FIG. 5) as well as a delay in the onset of temperature-driven coacervation as shown via Dynamic Light Scattering (DLS) (FIG. 6).

TABLE 1

| Concentration dependent transition temperatures for wild-type and fluorinated proteins | | |
|---|---|---|
| Conc. (mg/mL) | $CE_2$-RGD-TFL $T_t$ (° C.) | $CE_2$-RGD-wt $T_t$ (° C.) |
| 1.00 | 45.71 ± 0.51 | 41.60 ± 0.56 |
| 0.75 | 46.36 ± 0.03 | 42.48 ± 0.24 |
| 0.50 | 47.87 ± 0.72 | 44.16 ± 0.30 |
| 0.20 | 52.04 ± 0.84 | 47.32 ± 1.39 |

Figure 7:
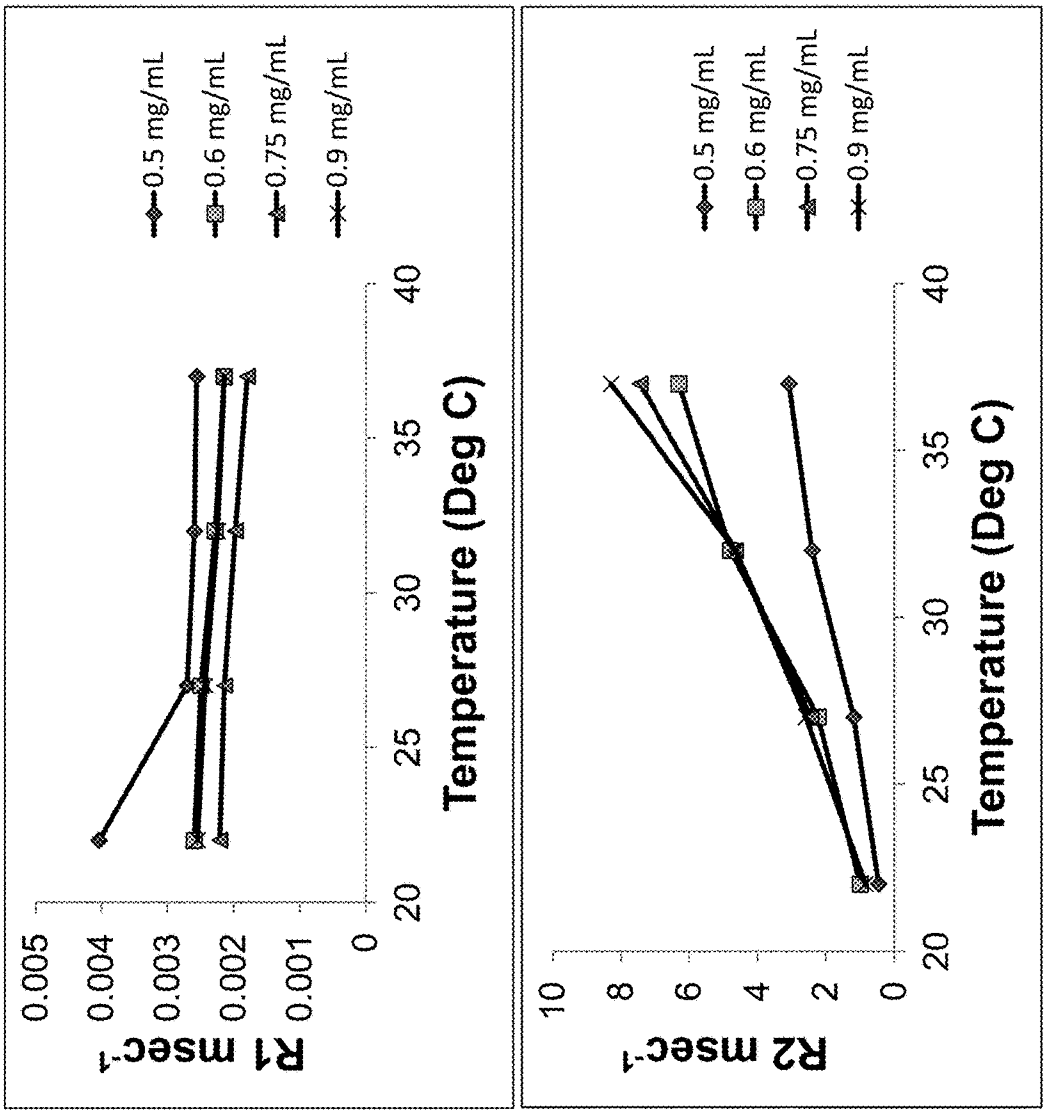
FIG. 7 is a representation of the nuclear magnetic resonance R1 and R2 relaxation times for the all fluorine atoms within the protein at varying concentrations and temperatures
Figure 12:
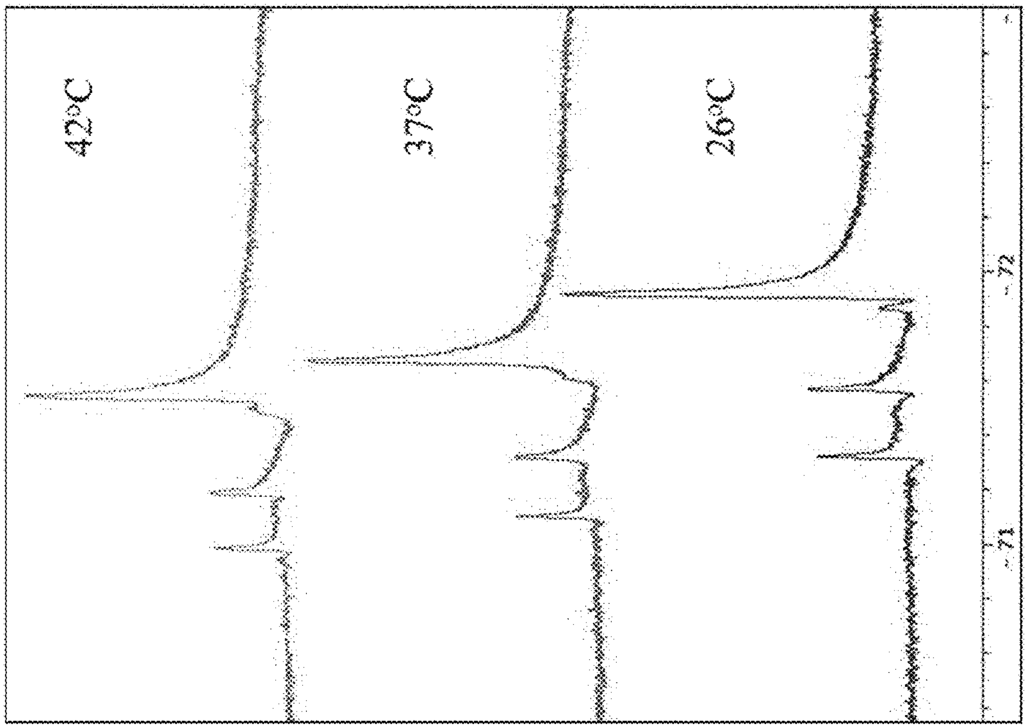
FIG. 12 is a representation of $^1$H decoupled $^{19}$F NMR of $CE_2$-RGD-TFL (1.2 mg/mL) at 26° C., 37° C. and 42° C., referenced with 0.01% para-fluorophenylalanine.

In order to investigate the magnetic resonance imaging potential of $CE_2$-RGD-TFL, the protein was subjected to inversion recovery and Car-Purcell-Meiboom-Gill (CPMG) and variable temperature 1D $^{19}F$ NMR experiments at 11.7-Tesla (See FIG. 12). Inversion recovery experiments show little change in R1 values, regardless of temperature or concentration but CPMG experiments reveal a remarkable dependence in $R_2$ values as a function of concentrations and temperatures (FIG. 7). When analyzing the $R_2/R_1$ as a function of concentration, there is support for using this protein as a $T_2$-nano-thermometer as it exhibits a consistent linear sensitivity within the 0.6 mg/mL to 0.9 mg/mL concentration range while peaking at −17000 at 0.75 mg/mL (Table 2). Incorporation of TFL in $CE_2$-RGD yields a drug carrier nanoparticle that can undergo temperature dependent structural changes measured by an increase in $R_2$ values, which leads us to believe that $CE_2$-RGD-TFL can be used as a T2-weighted MRI contrast agent. In this context, specific MRI pulse sequences or methods such as Ultrashort Echo Time (UTE) and Zero Echo Time (ZTE) MRI can thus enhance the signal generated from the protein at lesser fluorine concentrations.

TABLE 2

| Concentration dependent r2 and r1 values with r2/r1 ratio | | | |
|---|---|---|---|
| Conc. (mg/mL) | r2 | r1 | r2/r1 |
| 0.50 | 0.18 | −9.06E−05 | −2010 |
| 0.60 | 0.37 | −3.15E−05 | −11734 |
| 0.75 | 0.50 | −2.82E−05 | −17744 |
| 0.90 | 0.49 | −2.81E−05 | −17405 |

Figure 8:
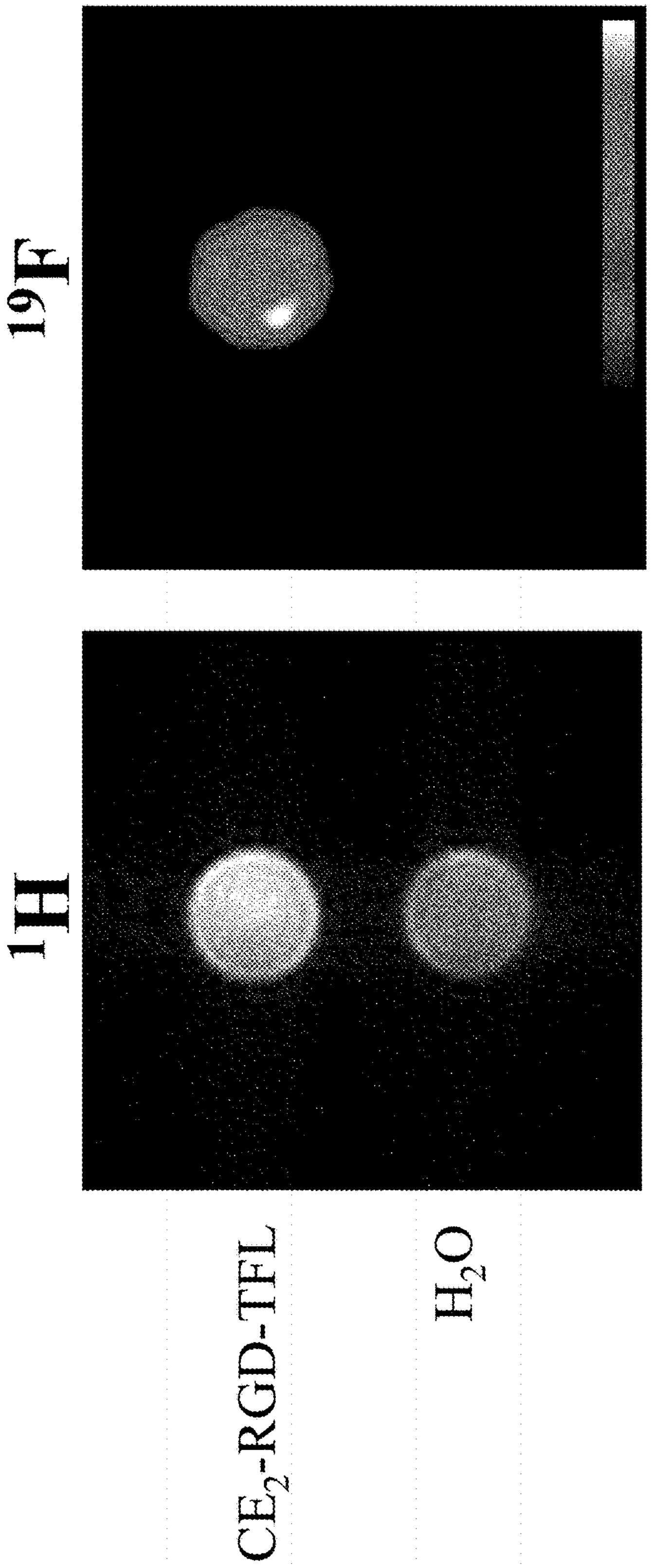
FIG. 8 is a representation of the magnetic resonance imaging portrayal after a gradient echo pulse sequence of the fluorinated protein and control water when the instrument scanner is tuned to either the proton ($^1$H) radiofrequency or the fluorine ($^{19}$F) radiofrequency

The 2D Gradient Echo MRI samples (referred to as phantoms) were subjected to an overnight (14 hours) cumulative scan in order to maximize $^{19}F$ signal. The negative control phantom was subjected to a significantly shorter scan time (2 seconds) due to the high $^{1}H$ signal inherent to water. Both the negative control and the $CE_2$-RGD-TFL phantoms elicited positive signals when the instrument was tuned to the $^{1}H$ radiofrequency (FIG. 8). Only the $CE_2$-RGD-TFL phantom yielded a positive signal when the instrument was tuned to the $^{19}F$ radio frequency (FIG. 8).

Figure 9:
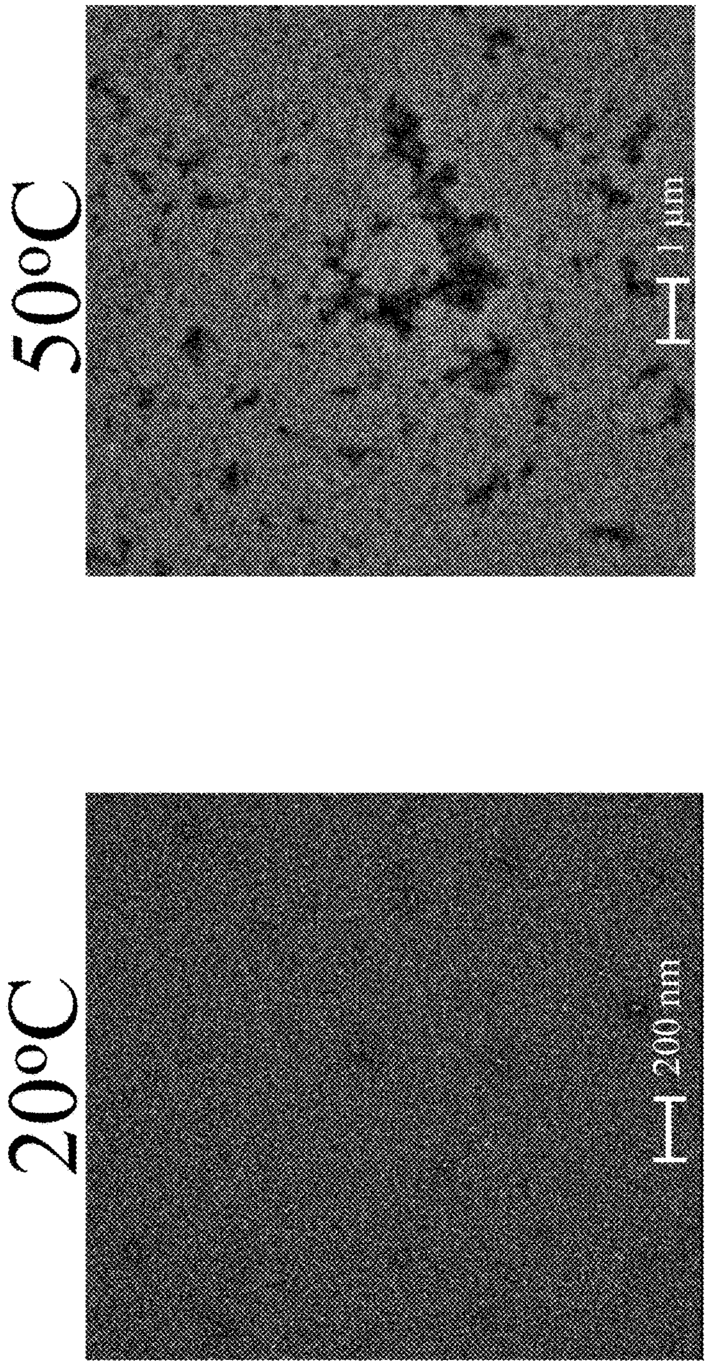
FIG. 9 is a representation of transmission electron micrographs of the fluorinated ($CE_2$-RGD-TFL) polymer carrier at the indicated temperatures.

Transmission electron microscopy images revealed a near homogenous population of $CE_2$-RGD-TFL particles 30 nm in diameter when the protein was subjected to a 1.5 hour incubation at 20° C. (FIG. 9). Conversely, when $CE_2$-RGD-TFL was subjected to a 50° C. for 1.5 hours, TEM images showed amorphous aggregates of no discernible uniformity in size (FIG. 9).

While the method has been described through specific embodiments, routine modifications will be apparent to those skilled in the art, which modifications are intended to be within the scope of the disclosure.

What is claimed is:

1. A protein polymer comprising from N- to C-terminus:

a coiled coil domain of cartilage oligomeric matrix protein (COMPcc) or a variant thereof selected from the group consisting of SEQ ID NOs: 3-14;

a linker sequence up to 30 amino acids, wherein the linker sequence comprises RGD and AT repeats and the RGD is directly N-terminal to the first AT repeat; and an elastin-like peptide domain comprising the sequence $[(VPGXG)_2VPGXG(VPGXG)_2]_n$ (SEQ ID NO:30), wherein n can be from 2 to 24, and X is any amino acid other than proline, wherein one or more leucine residues in the protein polymer are fluorinated.

2. A protein polymer comprising from the N- to the C-terminus:

an N-terminal sequence comprising a polyhistidine sequence;

a linker sequence comprising RGD and AT repeats, wherein the RGD is directly N-terminal to the first AT repeat sequence;

a coiled coil domain of cartilage oligomeric matrix protein (COMPcc) or a variant thereof selected from the group consisting of SEQ ID NOs: 3-14;

a linker sequence up to 30 amino acids and comprising RGD and AT repeats, wherein the RGD is directly N-terminal to the first AT repeat; and an elastin-like peptide sequence comprising the sequence $[(VPGXG)_2VPGXG(VPGXG)_2]_n$ (SEQ ID NO:30), wherein n can be from 2 to 24, and X is any amino acid other than proline, wherein one or more leucine residues in the protein polymer are fluorinated.

3. The protein polymer of claim 2, further comprising a C-terminal sequence after the elastin-like peptide.

4. The protein polymer of claim 1, wherein one or more fluorinated leucines are independently at each location monofluorinated, difluorinated, trifluorinated, tetrafluorinated, pentafluorinated or hexafluorinated.

5. The protein polymer of claim 1, wherein X is V.

6. The protein polymer of claim 1, wherein X is independently at each occurrence V or F.

7. The protein polymer of claim 1, wherein all leucine residues are trifluorinated.

8. The protein polymer of claim 1, wherein the elastin-like peptide domain sequence comprises $[(VPGVG)_2VPGFG(VPGVG)_2]_n$ (SEQ ID NO:31).

9. The protein polymer of claim 2, wherein the protein polymer has the sequence of SEQ ID NO:18, and wherein at least one leucine is fluorinated.

10. The protein polymer of claim 9, wherein all the leucine residues are fluorinated.

11. The protein polymer of claim 10, wherein the fluorinated leucine residues are independently at each location monofluorinated, difluorinated, trifluorinated, tetrafluorinated, pentafluorinated, or hexafluorinated.

12. The protein polymer of claim 11, wherein all the leucine residues are trifluorinated.

13. The protein polymer of claim 1, further comprising an agent encapsulated in the protein polymer.

14. The protein polymer of claim 13, wherein the encapsulated agent is doxorubicin.

15. A composition comprising the protein polymer of claim 13 in a pharmaceutically acceptable carrier.

16. A method for targeted delivery of an agent to integrin-expressing cancer cells for therapy and/or imaging comprising:

a) administering to an individual a composition of claim 15; and b) increasing the temperature of the targeted location to 38° C. to 42° C. thereby releasing the agent from the protein polymer at the targeted location, wherein the targeting is achieved by the binding of RGD sites on the protein polymer to integrin molecules expressed on the cancer cells.

17. The method of claim 16, further comprising the step of tracking the transport of the composition after administration of the composition to an individual, wherein the tracking is done by imaging of fluorinated leucines.

18. The method of claim 17, wherein the imaging is done by magnetic resonance imaging.

19. The method of claim 16, wherein the protein polymer in the composition has the sequence of SEQ ID NO:18.

20. The method of claim 19, wherein all the leucine residues are trifluorinated.

21. The method of claim 16, wherein the agent is a therapeutic agent.

22. The method of claim 16, wherein the agent is a diagnostic agent.

* * * * *

SEQUENCE LISTING

```
<160> NUMBER OF SEQ ID NOS: 32

<210> SEQ ID NO 1
<211> LENGTH: 61
<212> TYPE: PRT
<213> ORGANISM: artificial sequence
<220> FEATURE:
<223> OTHER INFORMATION: COMPcc uswith  N-terminal histidine tag

<400> SEQUENCE: 1

Met Arg Gly Ser His His His His His His Gly Ser Gly Asp Leu Ala
1               5                   10                  15

Pro Gln Met Leu Arg Glu Leu Gln Glu Thr Asn Ala Ala Leu Gln Asp
            20                  25                  30

Val Arg Glu Leu Leu Arg Gln Gln Val Lys Glu Ile Thr Phe Leu Lys
        35                  40                  45

Asn Thr Val Met Glu Cys Asp Ala Cys Gly Lys Leu Asn
    50                  55                  60


<210> SEQ ID NO 2
<211> LENGTH: 46
<212> TYPE: PRT
<213> ORGANISM: artificial sequence
<220> FEATURE:
<223> OTHER INFORMATION: coiled-coil region of COMP

<400> SEQUENCE: 2

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
```

```
            20                  25                  30

Thr Phe Leu Lys Asn Thr Val Met Glu Cys Asp Ala Cys Gly
        35                  40                  45


<210> SEQ ID NO 3
<211> LENGTH: 46
<212> TYPE: PRT
<213> ORGANISM: artificial sequence
<220> FEATURE:
<223> OTHER INFORMATION: COMPcc wild type sequence

<400> SEQUENCE: 3

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Cys Asp Ala Cys Gly
        35                  40                  45


<210> SEQ ID NO 4
<211> LENGTH: 46
<212> TYPE: PRT
<213> ORGANISM: artificial sequence
<220> FEATURE:
<223> OTHER INFORMATION: COMPcc variant

<400> SEQUENCE: 4

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45


<210> SEQ ID NO 5
<211> LENGTH: 46
<212> TYPE: PRT
<213> ORGANISM: artificial sequence
<220> FEATURE:
<223> OTHER INFORMATION: COMPcc variant

<400> SEQUENCE: 5

Gly Asp Leu Ala Pro Gln Met Leu Arg Glu Ala Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45


<210> SEQ ID NO 6
<211> LENGTH: 46
<212> TYPE: PRT
<213> ORGANISM: artificial sequence
<220> FEATURE:
<223> OTHER INFORMATION: COMPcc variant

<400> SEQUENCE: 6

Gly Asp Leu Ala Pro Gln Met Leu Arg Glu Leu Gln Glu Ala Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
```

35 40 45

<210> SEQ ID NO 7
<211> LENGTH: 46
<212> TYPE: PRT
<213> ORGANISM: artificial sequence
<220> FEATURE:
<223> OTHER INFORMATION: COMPcc variant

<400> SEQUENCE: 7

Gly Asp Leu Ala Pro Gln Met Leu Arg Glu Leu Gln Glu Thr Asn Ala
1 5 10 15

Ala Ala Gln Asp Val Arg Glu Leu Leu Arg Gln Gln Val Lys Glu Ile
20 25 30

Thr Phe Leu Lys Asn Thr Val Met Glu Ser Asp Ala Ser Gly
35 40 45

<210> SEQ ID NO 8
<211> LENGTH: 46
<212> TYPE: PRT
<213> ORGANISM: artificial sequence
<220> FEATURE:
<223> OTHER INFORMATION: COMPcc variant

<400> SEQUENCE: 8

Gly Asp Leu Ala Pro Gln Met Leu Arg Glu Leu Gln Glu Thr Asn Ala
1 5 10 15

Ala Leu Gln Asp Ala Arg Glu Leu Leu Arg Gln Gln Val Lys Glu Ile
20 25 30

Thr Phe Leu Lys Asn Thr Val Met Glu Ser Asp Ala Ser Gly
35 40 45

<210> SEQ ID NO 9
<211> LENGTH: 46
<212> TYPE: PRT
<213> ORGANISM: artificial sequence
<220> FEATURE:
<223> OTHER INFORMATION: COMPcc variant

<400> SEQUENCE: 9

Gly Asp Leu Ala Pro Gln Met Leu Arg Glu Leu Gln Glu Thr Asn Ala
1 5 10 15

Ala Leu Gln Asp Val Arg Glu Leu Ala Arg Gln Gln Val Lys Glu Ile
20 25 30

Thr Phe Leu Lys Asn Thr Val Met Glu Ser Asp Ala Ser Gly
35 40 45

<210> SEQ ID NO 10
<211> LENGTH: 46
<212> TYPE: PRT
<213> ORGANISM: artificial sequence
<220> FEATURE:
<223> OTHER INFORMATION: COMPcc variant

<400> SEQUENCE: 10

Gly Asp Leu Ala Pro Gln Met Leu Arg Glu Leu Gln Glu Thr Asn Ala
1 5 10 15

Ala Leu Gln Asp Val Arg Glu Leu Leu Arg Gln Ala Val Lys Glu Ile
20 25 30

Thr Phe Leu Lys Asn Thr Val Met Glu Ser Asp Ala Ser Gly
35 40 45

-continued

```
<210> SEQ ID NO 11
<211> LENGTH: 46
<212> TYPE: PRT
<213> ORGANISM: artificial sequence
<220> FEATURE:
<223> OTHER INFORMATION: COMPcc Variant

<400> SEQUENCE: 11

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ala
            20                  25                  30

Thr Phe Leu Lys Asn Thr Val Met Glu Ser Asp Ala Ser Gly
        35                  40                  45


<210> SEQ ID NO 12
<211> LENGTH: 46
<212> TYPE: PRT
<213> ORGANISM: artificial sequence
<220> FEATURE:
<223> OTHER INFORMATION: COMPcc variant

<400> SEQUENCE: 12

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Ala Lys Asn Thr Val Met Glu Ser Asp Ala Ser Gly
        35                  40                  45


<210> SEQ ID NO 13
<211> LENGTH: 46
<212> TYPE: PRT
<213> ORGANISM: artificial sequence
<220> FEATURE:
<223> OTHER INFORMATION: COMPcc variant

<400> SEQUENCE: 13

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Ala Met Glu Ser Asp Ala Ser Gly
        35                  40                  45


<210> SEQ ID NO 14
<211> LENGTH: 46
<212> TYPE: PRT
<213> ORGANISM: artificial sequence
<220> FEATURE:
<223> OTHER INFORMATION: COMPcc variant

<400> SEQUENCE: 14

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ala Asp Ala Ser Gly
        35                  40                  45


<210> SEQ ID NO 15
<211> LENGTH: 5
<212> TYPE: PRT
```

<213> ORGANISM: artificial sequence
<220> FEATURE:
<223> OTHER INFORMATION: E- domain segment
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Val Pro Gly Xaa Gly
1 5

<210> SEQ ID NO 16
<211> LENGTH: 5
<212> TYPE: PRT
<213> ORGANISM: artificial sequence
<220> FEATURE:
<223> OTHER INFORMATION: Artificial E domain sequence

<400> SEQUENCE: 16

Val Pro Gly Val Gly
1 5

<210> SEQ ID NO 17
<211> LENGTH: 6
<212> TYPE: PRT
<213> ORGANISM: artificial sequence
<220> FEATURE:
<223> OTHER INFORMATION: Histidine tag

<400> SEQUENCE: 17

His His His His His His
1 5

<210> SEQ ID NO 18
<211> LENGTH: 166
<212> TYPE: PRT
<213> ORGANISM: artificial sequence
<220> FEATURE:
<223> OTHER INFORMATION: Synthetic peptide

<400> SEQUENCE: 18

Met Arg Gly Ser His His His His His His Gly Ser Ala Cys Glu Leu
1 5 10 15

Ala Ala Arg Gly Asp Ala Thr Ala Thr Ala Thr Ala Thr Ala Ala Cys
20 25 30

Gly Asp Leu Ala Pro Gln Met Leu Arg Glu Leu Gln Glu Thr Asn Ala
35 40 45

Ala Leu Gln Asp Val Arg Glu Leu Leu Arg Gln Gln Val Lys Glu Ile
50 55 60

Thr Phe Leu Lys Asn Thr Val Met Glu Ser Asp Ala Ser Gly Leu Gln
65 70 75 80

Ala Ala Arg Gly Asp Ala Thr Ala Thr Ala Thr Ala Thr Ala Val Asp
85 90 95

Lys Pro Ile Ala Ala Ser Ala Val Pro Gly Val Gly Val Pro Gly Val
100 105 110

Gly Val Pro Gly Phe Gly Val Pro Gly Val Gly Val Pro Gly Val Gly
115 120 125

Val Pro Gly Val Gly Val Pro Gly Val Gly Val Pro Gly Phe Gly Val
130 135 140

Pro Gly Val Gly Val Pro Gly Val Gly Val Pro Leu Glu Gly Ser Gly
145 150 155 160

-continued

```
Thr Gly Ala Lys Leu Asn
                165


<210> SEQ ID NO 19
<211> LENGTH: 12
<212> TYPE: PRT
<213> ORGANISM: artificial sequence
<220> FEATURE:
<223> OTHER INFORMATION: Synthetic peptide

<400> SEQUENCE: 19

Met Arg Gly Ser His His His His His His Gly Ser
1               5                   10


<210> SEQ ID NO 20
<211> LENGTH: 46
<212> TYPE: PRT
<213> ORGANISM: artificial sequence
<220> FEATURE:
<223> OTHER INFORMATION: Synthetic peptide

<400> SEQUENCE: 20

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45


<210> SEQ ID NO 21
<211> LENGTH: 25
<212> TYPE: PRT
<213> ORGANISM: artificial sequence
<220> FEATURE:
<223> OTHER INFORMATION: Synthetic peptide

<400> SEQUENCE: 21

Leu Gln Ala Ala Arg Gly Asp Ala Thr Ala Thr Ala Thr Ala Thr Ala
1               5                   10                  15

Val Asp Lys Pro Ile Ala Ala Ser Ala
            20                  25


<210> SEQ ID NO 22
<211> LENGTH: 52
<212> TYPE: PRT
<213> ORGANISM: artificial sequence
<220> FEATURE:
<223> OTHER INFORMATION: Synthetic peptide

<400> SEQUENCE: 22

Val Pro Gly Val Gly Val Pro Gly Val Gly Val Pro Gly Phe Gly Val
1               5                   10                  15

Pro Gly Val Gly Val Pro Gly Val Gly Val Pro Gly Val Gly Val Pro
            20                  25                  30

Gly Val Gly Val Pro Gly Phe Gly Val Pro Gly Val Gly Val Pro Gly
        35                  40                  45

Val Gly Val Pro
    50


<210> SEQ ID NO 23
<211> LENGTH: 11
<212> TYPE: PRT
<213> ORGANISM: artificial sequence
<220> FEATURE:
```

<223> OTHER INFORMATION: Synthetic peptide

<400> SEQUENCE: 23

Leu Glu Gly Ser Gly Thr Gly Ala Lys Leu Asn
1 5 10

<210> SEQ ID NO 24
<211> LENGTH: 33
<212> TYPE: DNA
<213> ORGANISM: artificial sequence
<220> FEATURE:
<223> OTHER INFORMATION: Primer

<400> SEQUENCE: 24
gagctcgctg ctcgtggcga cgccactgct acg 33

<210> SEQ ID NO 25
<211> LENGTH: 33
<212> TYPE: DNA
<213> ORGANISM: artificial sequence
<220> FEATURE:
<223> OTHER INFORMATION: Primer

<400> SEQUENCE: 25
cgtagcagtg gcgtcgccac gagcagcgag ctc 33

<210> SEQ ID NO 26
<211> LENGTH: 33
<212> TYPE: DNA
<213> ORGANISM: artificial sequence
<220> FEATURE:
<223> OTHER INFORMATION: Primer

<400> SEQUENCE: 26
ctgcaggctg cccgtggcga cgctactgca acc 33

<210> SEQ ID NO 27
<211> LENGTH: 33
<212> TYPE: DNA
<213> ORGANISM: artificial sequence
<220> FEATURE:
<223> OTHER INFORMATION: Primer

<400> SEQUENCE: 27
ggttgcagta gcgtcgccac gggcagcctg cag 33

<210> SEQ ID NO 28
<211> LENGTH: 20
<212> TYPE: PRT
<213> ORGANISM: artificial sequence
<220> FEATURE:
<223> OTHER INFORMATION: synthetic protein

<400> SEQUENCE: 28

Ala Cys Glu Leu Ala Ala Arg Gly Asp Ala Thr Ala Thr Ala Thr Ala
1 5 10 15

Thr Ala Ala Cys
20

<210> SEQ ID NO 29
<211> LENGTH: 5
<212> TYPE: PRT
<213> ORGANISM: artificial sequence
<220> FEATURE:
<223> OTHER INFORMATION: synthetic protein

<400> SEQUENCE: 29

Val Pro Gly Phe Gly
1 5

<210> SEQ ID NO 30
<211> LENGTH: 25
<212> TYPE: PRT
<213> ORGANISM: Artificial Sequence
<220> FEATURE:
<223> OTHER INFORMATION: synthetic protein
<220> FEATURE:
<221> NAME/KEY: X
<222> LOCATION: (4)..(4)
<223> OTHER INFORMATION: X can be any amino acid
<220> FEATURE:
<221> NAME/KEY: X
<222> LOCATION: (9)..(9)
<223> OTHER INFORMATION: X can be any amino acid
<220> FEATURE:
<221> NAME/KEY: X
<222> LOCATION: (14)..(14)
<223> OTHER INFORMATION: X can be any amino acid
<220> FEATURE:
<221> NAME/KEY: X
<222> LOCATION: (19)..(19)
<223> OTHER INFORMATION: X can be any amino acid
<220> FEATURE:
<221> NAME/KEY: X
<222> LOCATION: (24)..(24)
<223> OTHER INFORMATION: X can be any amino acid

<400> SEQUENCE: 30

Val Pro Gly Xaa Gly Val Pro Gly Xaa Gly Val Pro Gly Xaa Gly Val
1 5 10 15

Pro Gly Xaa Gly Val Pro Gly Xaa Gly
20 25

<210> SEQ ID NO 31
<211> LENGTH: 25
<212> TYPE: PRT
<213> ORGANISM: Artificial Sequence
<220> FEATURE:
<223> OTHER INFORMATION: synthetic protein

<400> SEQUENCE: 31

Val Pro Gly Val Gly Val Pro Gly Val Gly Val Pro Gly Phe Gly Val
1 5 10 15

Pro Gly Val Gly Val Pro Gly Val Gly
20 25

<210> SEQ ID NO 32
<211> LENGTH: 52
<212> TYPE: PRT
<213> ORGANISM: Artificial Sequence
<220> FEATURE:
<223> OTHER INFORMATION: synthetic protein

<400> SEQUENCE: 32

Val Pro Gly Val Gly Val Pro Gly Val Gly Val Pro Gly Phe Gly Val
1 5 10 15

Pro Gly Val Gly Val Pro Gly Val Gly Val Pro Gly Val Gly Val Pro
20 25 30

Gly Val Gly Val Pro Gly Phe Gly Val Pro Gly Val Gly Val Pro Gly
35 40 45

Val Gly Val Pro
50